(12) United States Patent
Ohara

(10) Patent No.: US 7,155,048 B2
(45) Date of Patent: Dec. 26, 2006

(54) PCI RADIATION IMAGE PROCESSING APPARATUS, PCI RADIATION IMAGE DETECTING APPARATUS, PCI RADIATION IMAGE OUTPUTTING APPARATUS, AND PCI IMAGE DIAGNOSIS SUPPORTING APPARATUS

(75) Inventor: Hiromu Ohara, Hino (JP)

(73) Assignee: Konica Corporation, Tokyo (JP)

( * ) Notice: Subject to any disclaimer, the term of this patent is extended or adjusted under 35 U.S.C. 154(b) by 78 days.

(21) Appl. No.: 11/142,847

(22) Filed: May 31, 2005

(65) Prior Publication Data

US 2005/0213801 A1  Sep. 29, 2005

Related U.S. Application Data

(63) Continuation of application No. 09/843,079, filed on Apr. 27, 2001, now Pat. No. 6,934,409.

(30) Foreign Application Priority Data

Apr. 27, 2000 (JP) .............................. 2000/126819

(51) Int. Cl.
*G06K 9/00* (2006.01)
(52) U.S. Cl. .................. 382/132; 382/274; 378/37; 250/370.09
(58) Field of Classification Search ........ 382/128–134, 382/154, 156, 169, 172, 181, 203, 209–215, 382/224, 237, 255, 260, 274, 276, 291, 294, 382/300, 305; 378/28, 37, 98.6, 98.9, 146, 378/197; 250/370.09, 492.1
See application file for complete search history.

(56) References Cited

U.S. PATENT DOCUMENTS

| | | | | |
|---|---|---|---|---|
| 4,096,391 A | * | 6/1978 | Barnes | 378/146 |
| 5,982,953 A | * | 11/1999 | Yanagita et al. | 382/294 |
| 6,001,334 A | * | 12/1999 | Hirai | 424/9.411 |
| 6,071,491 A | * | 6/2000 | Epstein et al. | 424/1.49 |
| 6,196,715 B1 | * | 3/2001 | Nambu et al. | 378/197 |
| 6,226,353 B1 | * | 5/2001 | Wilkins et al. | 378/98.9 |
| 6,510,253 B1 | * | 1/2003 | Yamada | 382/300 |
| 6,594,335 B1 | * | 7/2003 | Davidson | 378/43 |
| 6,671,394 B1 | * | 12/2003 | Sako | 382/132 |

FOREIGN PATENT DOCUMENTS

| | | |
|---|---|---|
| EP | 0 599/097 A2 | 6/1994 |
| WO | WO 98/28950 | 7/1998 |

OTHER PUBLICATIONS

Partial European Search Report dated Dec. 22, 2005.
Gureyev, T.E., et al., "Hard x-ray quantitative non-interferometric phase-contrast microscopy," Journal of Physics D. Applied Physics, 32():563-567, Mar. 7, 1999.
Wong, Stephen T.C., et al., "A Hospital Integrated Framework for Multimodality Image Base Management," IEEE Transactions on Systems, Man and Cybernetics. Part A: Systems and Humans, 26(4):455-469, Jul. 1, 1996.

* cited by examiner

*Primary Examiner*—Jingge Wu
*Assistant Examiner*—Seyed Azarian
(74) *Attorney, Agent, or Firm*—Finnegan, Henderson, Farabow, Garrett & Dunner, L.L.P.

(57) ABSTRACT

A phase contrast radiographic image processing apparatus, comprises: a management information storing section to store management information regarding a radiography; and an image processing section to apply an image processing onto a phase contrast radiographic image produced by the phase contrast radiography, wherein the image processing section determines an image processing condition based on the management information stored in the management information storing section and conducts the image processing based on the determined image processing condition.

6 Claims, 26 Drawing Sheets

IMAGE SURFACE

EDGE SECTION OF IRRADIATED FIELD

INTERIOR OF IRRADIATED FIELD

EXTERIOR OF IRRADIATED FIELD

FIG. 17 (a)
FIG. 17 (b)
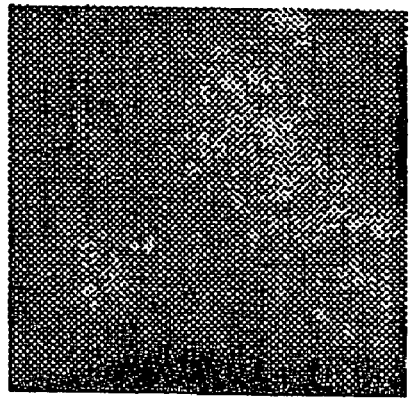
▲CLUSTERED MICROCALCIFICATION
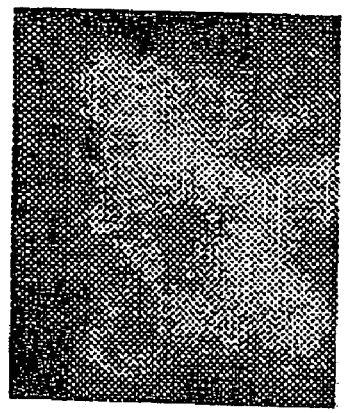
▲TUMOR

▲DISPLAYED IMAGE

DETECTION EXAMPLE OF mass

DETECTION EXAMPLE OF calc.

DETECTION EXAMPLE OF CLUSTERS

FIG. 24 (a)   FIG. 24 (b)
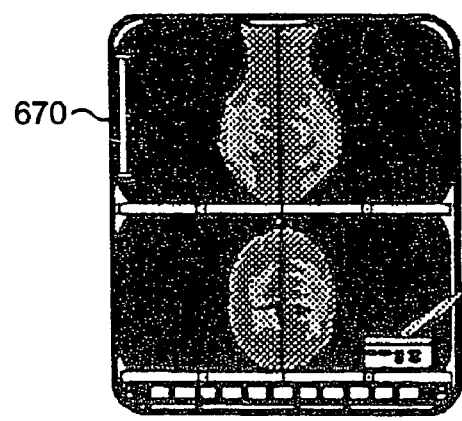
▲DISPLAYED IMAGE
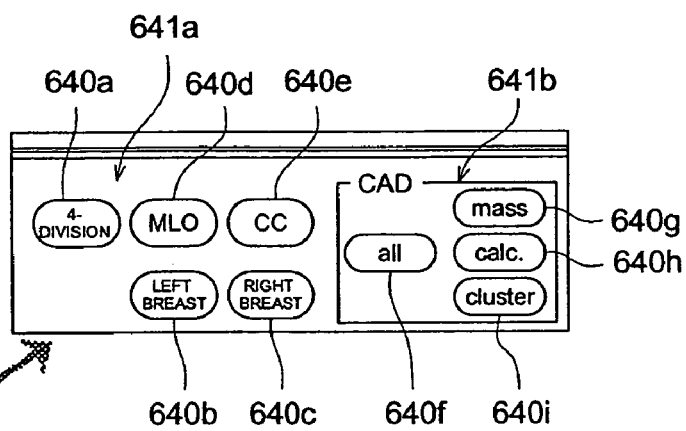

FIG. 26 (a)   FIG. 26 (b)   FIG. 26 (c)
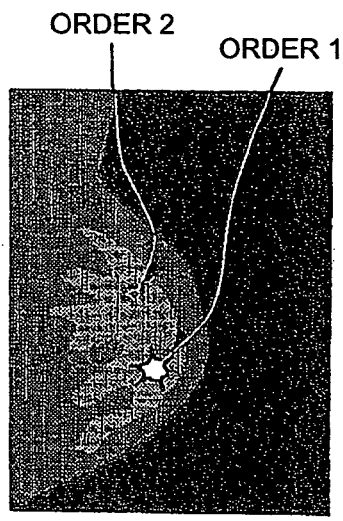
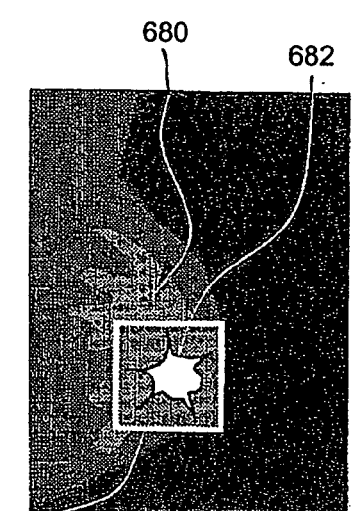
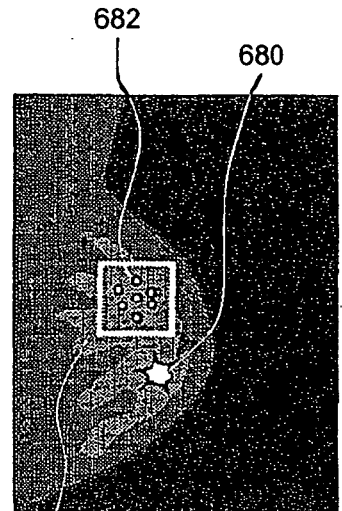
FIG. 26(a): ORDER 2, ORDER 1 — NO MAGNIFICATION FACTOR DISPLAY WINDOW →
FIG. 26(b): 680, 682 — MAGNIFICATION FACTOR OF ORDER 1 CANDIDATE (681) →
FIG. 26(c): 682, 680 — MAGNIFICATION FACTOR OF ORDER 2 CANDIDATE (681) → ...

PCI RADIATION IMAGE PROCESSING APPARATUS, PCI RADIATION IMAGE DETECTING APPARATUS, PCI RADIATION IMAGE OUTPUTTING APPARATUS, AND PCI IMAGE DIAGNOSIS SUPPORTING APPARATUS

This application is a continuation application of U.S. application Ser. No. 09/843,079, filed Apr. 27, 2001 now U.S. Pat. No. 6,934,409, the contents of which are incorporated herein by reference. That application claims the foreign priority benefit of Japanese Application No. 2000-126819, filed Apr. 27, 2000.

BACKGROUND OF THE INVENTION

The present invention relates to a PCI (phase contrast radiographic image) processing apparatus, a PCI detecting apparatus, a PCI outputting apparatus, and a PCI diagnosis supporting apparatus, all of which utilize radiation in the medical field.

Heretofore, radiation imaging apparatus capable of resulting in digital radiation images have been known, and include one in which stimulable phosphors are employed which accumulate some of radiation energy and results in stimulable emission corresponding to stored energy by irradiating excited light, a flat panel detector (FPD) in which electrical signals are formed corresponding to the dose of the irradiated radiation employing a plurality of two-dimensionally arranged sensors, and based on said electrical signals, image data are generated, and the like.

On the other hand, radiation images are shadow images produced by utilizing the difference in transmission of radiation, depending on the atomic weight of substances constituting an imaging object. Namely, the two-dimensional distribution of the amount of the radiation, which is radiated from the radiation source and transmitted through an imaging object to be radiographed, is detected utilizing a radiation image detector, and a radiation image is formed based on the radiation absorption contrast of said imaging object.

Incidentally, since said radiation is comprised of electromagnetic waves, it exhibits wave characteristics. Therefore, when it is transmitted through an imaging object, diffraction as well as refraction occurs, and it is possible to detect these as images.

In recent years, utilizing said properties, a method (radiography) to produce radiation images, which enhance the contrast of an imaging object, have been proposed, and said images are called phase contrast radiography-radiation images (radiation images produced by the phase contrast radiography) or refraction contrast-radiography radiation images. In said images, the contrast at the boundaries of an imaging object is enhanced and the detection properties of radiation images are improved. As a result, application to the medical fields, nondestructive test fields, and the like, in which such radiation is utilized, has been expected.

Incidentally, in phase contrast radiographic images, in the same manner as ordinary radiography-radiation images, as described above, it is possible to obtain digital phase contrast radiographic images by directly forming digital images or by digitizing analog images employing a scanner and the like. Since such phase contrast radiographic images, comprised of digital images, are different from those produced by utilizing ordinary image capturing, an optimal image processing method, which is different from that for the images produced by ordinary image capturing, is required.

Further, there is a possibility of a novel energy subtraction method utilizing the phase contrast radiographic images. Further, since the phase contrast radiographic images are magnified, it is required to output images in a size which is readily utilized for diagnosis. Still further, there is a possibility to enhance the diagnosis supporting accuracy, utilizing phase contrast radiographic images.

From the view of the foregoing, the present invention has been accomplished. An object of the present invention is to provide a phase contrast radiographic image processing apparatus capable of optimally processing phase contrast radiographic images and a phase contrast radiographic image detecting apparatus. Another object of the present invention is to provide a phase contrast radiographic image processing apparatus capable of improving the image quality of energy subtraction. Still another object of the present invention is to provide a phase contrast radiographic image outputting apparatus capable of carrying out suitable image output of phase contrast radiographic images. A further object of the present invention is to provide a phase contrast radiographic image diagnosis supporting apparatus capable of improving the accuracy of diagnosis support.

In order to overcome said problems and to accomplish the aforementioned imaging objects, the embodiments of the present invention are as follows:

The present invention is a phase contrast radiographic image processing apparatus comprising an image processing means which applies image processing to said phase contrast radiographic image.

The present invention is a phase contrast radiographic image detection processing apparatus comprising a radiation image detecting means which outputs image signals corresponding to a captured phase contrast radiographic image, as well as an image processing means which applies image processing to said image signals outputted from said radiation image detecting means.

In said phase contrast radiographic image processing apparatus and phase contrast radiographic image detection processing apparatus, an image processing means comprises a phase contrast radiographic image processing means which applies image processing to a phase contrast radiographic image, and also comprises an ordinarily captured image processing means which applies image processing to an ordinarily captured image.

Further, said image processing means comprises a radiography information storing means which stores management information regarding said imaging. Said image processing means determines image processing conditions, utilizing information regarding radiography stored in a radiography information storing means, and can carry out processing based on said conditions. Further, said image processing means comprises a region of interest setting means which sets the desired region of interest upon analyzing said phase contrast radiographic image, and determines image processing conditions based on image signals in the set region of interest, and makes it possible to carry out processing based on the determined conditions.

Further, said image processing means comprises a gradation processing means which carries out processing which converts gradation.

Further, said processing means comprises a gradation conversion curve storing means. Said gradation processing means can select a gradation conversion curve from a plurality of gradation conversion curves stored in said gradating converting curve storing means, and can carry out processing which converts gradation based on the selected gradation conversion curve.

In said gradation processing means, it is possible to select a gradation conversion curve from a plurality of gradation reconverting curves stored in said gradation conversion curve storing means based on management information regarding radiography.

Said image processing means comprises a basic gradation conversion curve storing means. In said gradation processing means, any basic gradation conversion curve is selected from a plurality of basic gradation conversion curves stored in said basic gradation conversion curve storing means, and the desired gradation conversion curve is prepared by modifying the selected basic gradation conversion curve. Based on the prepared gradation conversion curve, it is possible to carry out processing which converts gradation.

In said gradation processing means, based on the management information regarding radiography from a plurality of basic gradation conversion curves stored in said basic gradation conversion curve storing means, it is possible to select a basic gradation conversion curve.

In said gradation processing means, it is possible to carry out processing under the conditions in which a contrast coefficient with respect to a phase contrast radiographic image is smaller than that with respect to an ordinarily captured image.

Said image processing means comprises a frequency enhancement processing means which carries out frequency enhancement processing. In said frequency enhancement processing, the degree of enhancement, with respect to a phase contrast radiographic image, is smaller than said frequency enhancement coefficient with respect to an ordinarily captured image. Further, in said frequency enhancement processing, frequency enhancement processing conditions are determined based on the management information regarding radiography, and it is possible to carry out processing based on the determined conditions.

Said image processing means comprises a dynamic range compression processing means which carries out dynamic range compression processing. In said dynamic compression range processing, the degree of correction, with respect to a phase contrast radiographic image, is greater than the coefficient with respect to an ordinarily captured image. In said dynamic range compression processing, dynamic compression processing conditions are determined based on management information regarding radiography, and it is possible to carry out processing based on the determined conditions.

The present invention is a phase contrast radiographic image processing apparatus comprising a subtraction processing means in which a plurality of radiation images, including at least one phase contrast radiographic image which is obtained by capturing the same imaging object, is subjected to subtraction processing and a subtraction image is obtained.

In said phase contrast radiographic image processing apparatus, a plurality of radiation images are captured by one time X-ray irradiated, and it is possible to obtain a subtraction image employing said image. Further, it is possible to place a filter comprising low energy radiation component absorbing materials at least one position interposed between each detector. Further, said phase contrast radiographic image processing apparatus comprises a weighting means which applies the specified weighting to a plurality of obtained images. Said phase contrast radiographic image processing apparatus also comprises a size and position matching processing means which matches sizes and positions of a plurality of images.

Further, said phase contrast radiographic image processing apparatus comprises a radiography information storing means. When management information regarding radiography includes a magnification factor, the sizes of a plurality of images are matched employing said a magnification factor information as well as interpolation processing. Thus, it is possible thereafter to carry out position matching processing. Further, said CPI radiation image processing apparatus comprises a captured image storing means which stores management information regarding radiography. When said management information regarding radiography includes no magnification factor, said magnification factor is obtained based on the analysis results, and the sizes of plurality of images are matched based on the obtained magnification factor and interpolation processing. Thus, it is thereafter possible to carry out position matching processing.

The present invention is a phase contrast radiographic image processing apparatus comprising an addition processing means in which a plurality of radiation images, including at least one phase contrast radiographic image which is obtained by capturing the same imaging object, is subjected to addition processing and an addition image is obtained.

In said phase contrast radiographic image processing apparatus, a plurality of radiation images are captured by single X-ray irradiation, and it is possible to obtain an addition image employing said images. Further, said phase contrast radiographic image processing apparatus comprises a weighting means which applies a specified weighting to a plurality of obtained images. Said phase contrast radiographic image processing apparatus also comprises a size and position matching processing means which matches sizes and positions of a plurality of images.

Further, said phase contrast radiographic image processing apparatus comprises a radiography information storing means. When management information regarding radiography includes magnification factors, the sizes of a plurality of images are matched employing said magnification factor information as well as interpolation processing. Thus, it is thereafter possible to carry out a position matching processing. Further, said CPI radiation image processing apparatus comprises a captured image storing means which stores management information regarding radiography. When said management information regarding radiography includes no a magnification factor, said magnification factor is obtained based on the analyzed results, and the sizes of plurality of images are matched based on the obtained magnification factor and optional interpolation processing. Thus, it is possible thereafter to carry out position matching processing.

The present invention is a phase contrast radiographic image outputting apparatus comprising an outputting means which outputs phase contrast radiographic images captured at a magnification factor under a reduction ratio α of 1 or less.

Said phase contrast radiographic image outputting apparatus comprises an interpolation processing condition storing means which stores a plurality of interpolation processing conditions. In said outputting means, it is possible to output said phase contrast radiographic images in such a manner that any interpolation processing conditions are selected from a plurality of interpolation processing conditions stored in said interpolation processing condition storing means and interpolation processing is carried out utilizing the selected interpolation processing condition.

Said interpolation processing utilizes at least nearest neighbor interpolation processing, straight-line interpolation processing, spline interpolation processing, cubic-convolution interpolation processing, or bell-spline interpolation processing.

Said CPI image processing apparatus comprises a radiography information storing means, and determines interpolation processing conditions based on the management information regarding radiography, and can carry out interpolation processing based on the determined conditions.

Interpolation processing is carried out based on the information of the sampling pitch of an inputting means, the sampling pitch of an outputting means, and the image magnification factor, and captured images are outputted under the same magnification factor. Further, of the management information regarding radiography, it is possible to output specified information while attached to outputted images.

The present invention is a phase contrast radiographic image diagnosis supporting apparatus comprising an image storing means which stores phase contrast radiographic image data and an abnormal shadow image candidate detecting means which detects abnormal shadow candidates. In said phase contrast radiographic image diagnosis supporting apparatus it is possible to comprise an image displaying means which displays stored phase contrast radiographic image data as well as abnormal shadow candidates.

The present invention is a phase contrast radiographic image diagnosis supporting apparatus which comprises a subtraction processing means in which a plurality of radiation images, including at least one phase contrast radiographic image, which is obtained by capturing the same imaging object, is subjected to subtraction processing and a subtraction image is obtained, and an abnormal shadow candidate detecting means which detects abnormal shadow candidates by analyzing said subtraction images.

Said phase contrast radiographic image diagnosis supporting apparatus is comprised of an image displaying means which displays stored phase contrast radiographic image data as well as said detected abnormal shadow candidates. Further, a plurality of radiation images is captured employing single X-ray irradiation and it is possible to obtain subtraction images from said images. It is possible to place a filter comprising low energy radiation component absorbing materials at least one position interposed between each detector.

Further, said phase contrast radiographic image diagnosis supporting apparatus comprises a weighting means which applies the specified weighting to a plurality of obtained images, and is also capable of comprising a size and position matching processing means which matches sizes and positions of a plurality of images.

Further, said phase contrast radiographic image diagnosis supporting apparatus comprises a radiography information storing means which stores management information regarding radiography. When management information regarding radiography includes a magnification factor, the sizes of a plurality of images are matched employing said a magnification factor information as well as interpolation processing. Thus, thereafter, it is possible to carry out a position matching processing. Further, said phase contrast radiographic image diagnosis supporting apparatus comprises a radiography information storing means which stores management information regarding radiography. When said management information regarding radiography includes no magnification factor, said magnification factor is obtained based on the analyzed results, and the sizes of a plurality of images are matched based on the obtained magnification factor and optional interpolation processing. It is then possible to carry out position matching processing.

The present invention is also a phase contrast radiographic image diagnosis supporting apparatus which comprises an addition processing means in which a plurality of radiation images including at least one phase contrast radiographic image, which is obtained by capturing an image of the same imaging object, is subjected to addition processing and an addition image is obtained, as well as an abnormal shadow candidate detecting means which detects abnormal shadow candidates by analyzing said addition images.

Said phase contrast radiographic image diagnosis supporting apparatus is capable of comprising said image displaying means which displays stored phase contrast radiographic image data as well as said detected abnormal shadow candidates. A plurality of radiation images is captured employing single X-ray irradiation, and it is possible to obtain addition images from said images.

Further, said phase contrast radiographic image diagnosis supporting apparatus comprises a weighting means which applies the specified weighting to a plurality of obtained images, and is also capable of comprising a size and position matching processing means which matches sizes and positions of a plurality of images.

Said phase contrast radiographic image diagnosis supporting apparatus comprises a radiography information storing means which stores management information regarding radiography. When management information regarding radiography includes magnification factors, the sizes of a plurality of images are matched employing said magnification factor information as well as interpolation processing. It is then possible to thereafter carry out a position matching processing. Further, said phase contrast radiographic image diagnosis supporting apparatus comprises a radiography information storing means which stores management information regarding radiography. When said management information regarding radiography includes no magnification factor, said magnification factor is obtained based on the analyzed results, and the sizes of plurality of images are matched based on the obtained magnification factor and optional interpolation processing. It is then possible to thereafter carry out position matching processing.

BRIEF DESCRIPTION OF THE DRAWINGS

FIGS. 17(a) and 17(b) show images illustrating the detection of microcalcification clusters and tumor shadows, respectively.

FIGS. 24(a) and 24(b) are views in which a scale is attached to the image.

FIGS. 26(a) to 26(c) show a series of views by switching a display having no magnification factor display window, a display which shows an abnormal shadow candidate in the first order under magnification factor, and a display which shows an abnormal shadow candidate in the second order under magnification factor.

DETAILED DESCRIPTION OF THE PREFERRED EMBODIMENTS

Figure 1:
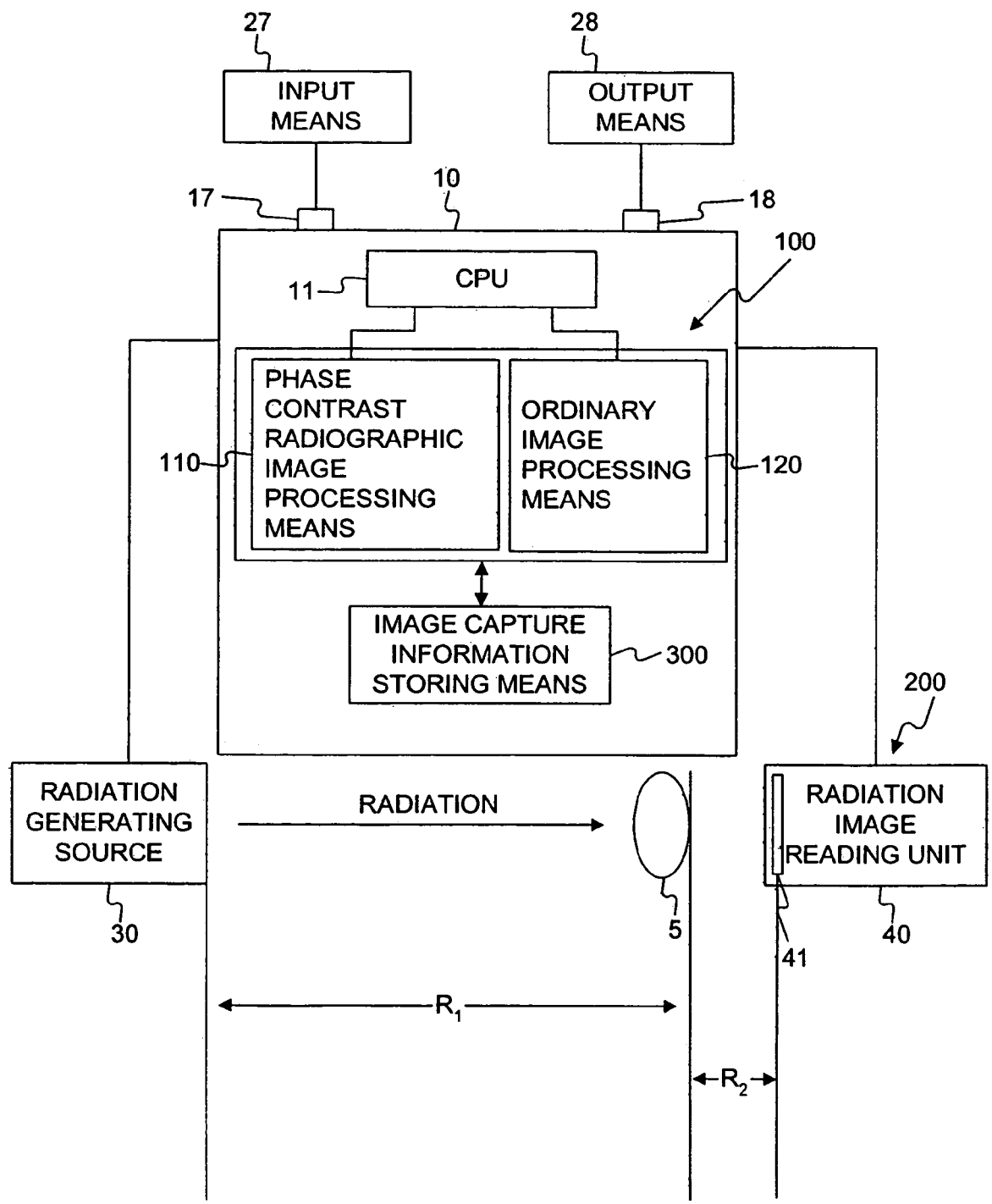
FIG. 1 is a diagram showing the constitution of a phase contrast radiographic image processing apparatus.

The embodiments of the phase contrast radiographic image processing apparatus, the phase contrast radiographic image detection processing apparatus, the phase contrast radiographic image outputting apparatus, and the phase contrast radiographic image diagnosis supporting apparatus of the present invention will now be detailed with reference to the drawings. However, the present invention is not limited to these embodiments.

Employed in the phase contrast radiographic image processing apparatus, a phase contrast radiographic image detection processing apparatus, a phase contrast radiographic image outputting apparatus, and a phase contrast radiographic image diagnosis supporting apparatus of the present invention, are phase contrast radiographic images comprised of digital data. Said CPI radiation images may be obtained either directly as digital images or upon digitizing the same.

Said phase contrast radiographic images are those obtained by capturing images employing apparatus, and the like, disclosed in Japanese Patent Application Nos. 11-203969, 11-266605, 2000-44381, and 2000-5266605, and also images obtained by utilizing radiography methods and the like disclosed in Japanese Patent Application Nos. 11-203969, 11-200005, and 2000-44381.

The apparatus described in Japanese Patent Application No. 11-203069 is an X-ray image capturing apparatus constituted as described below. Said apparatus comprises an X-ray tube having a focal spot size (Dμm) of at least 30 μm, a means which fixes an imaging object position, and an X-ray detecting unit. Further, it is possible that distance R1 (in m) from said X-ray tube to an imaging object fixed with said fixing means, be maintained in the range represented by the formula of $R1 \geq (D-7)/200$ (in m), and distance R2, from said imaging object fixed with said fixing means to said X-ray detecting unit be maintained at no less than 0.15 m.

Further, the method described in Japanese Patent Application No. 11-203969 is an X-ray image capturing method, as described below. An X-ray image, which is formed by allowing X-rays generated by an X-ray tube to transmit an imaging object, is detected by an X-ray detector, and sharpness degraded by penumbras is enhanced utilizing image edge enhancement using refraction contrast enhancement.

Further, said X-ray image capturing method utilizes an X-ray tube having a focal spot size (Dμm) of at least 30 μm.

Further, in said X-ray image capturing method, images are captured in such a manner that distance R1 (in m) from said X-ray tube to said imaging object is maintained in the range represented by the formula of $R1 \geq (D-7)/200$ (in m), and distance R2 from said imaging object to said X-ray detector is at least 0.15 m.

The apparatus as well as the method described in the aforementioned Japanese Patent Application No. 11-203969 comprises more preferable embodiments such that: said distance R1 is in the range of $10 > R1 \geq (D-7)/200$ (in m) and further in the range of $0.7 \leq R1 \leq 5$ (in m); said X-ray tube has a focal spot size of from 30 to 1,000 μm and further from 50 to 500 μm; the energy of bright line spectrum of X-rays irradiated onto said imaging object is from 10 keV to 60 keV; the anode of said X-ray tube is comprised of molybdenum or rhodium; the pixel size of said X-ray detector is from 1 to 200 μm; and the like.

The apparatus described in Japanese Patent Application No. 2000-44381 is an X-ray image capturing apparatus which comprises an X-ray tube which emits divergent X-rays, an imaging object fixing member which is employed to fix an imaging object with respect to said X-ray tube, and an X-ray image detector which detects X-ray images which transmit said imaging object. When magnifying X-ray radiography is carried out by transmitting X-rays emitted from said X-ray tube through said imaging object, it is possible to arrange said imaging object fixing member and said X-ray image detector so that the formula of $9E \leq B$ is held, wherein E (in μm) represents edge enhancement width due to X-ray diffraction contrast, and B (in μm) represents the blurring width due to the penumbra of said X-ray image.

Further, the method described in Japanese Patent Application No. 2000-44381 is an X-ray image capturing method in which an X-ray tube is employed which radiates divergent X-rays; magnifying X-ray radiography is carried out by transmitting X-rays emitted from said X-ray tube through said imaging object; and $9E \leq B$ is held, wherein E (in μm) represents edge enhancement width due to X-ray diffraction contrast, and B (in μm) represents the blurring width due to the penumbra of said X-ray image.

The apparatus as well as the method described in the aforementioned Japanese Patent Application No. 2000-44381 comprises more preferable embodiments such that: distance R1 between said X-ray tube and said imaging object is at least 0.5 m; distance R2 between said imaging object and said X-ray image detector is at least 1 m and said R1+ said R2 is no more than 5 m; said magnifying X-ray radiography is at a factor of 1.0 to 10; the focal spot size of said X-ray tube is from 10 to 1,000 µm and more preferably from 30 to 300 µm; the set tube voltage of X-rays emitted onto said imaging object is from 50 to 150 kVp; said X-ray tube is a tungsten rotation cathode X-ray tube; the pixel size of said X-ray detector is from 1 to 200 µm; and the like.

Further, it is possible to express the aforementioned edge enhancement width, "E", for example, utilizing three formulas described below:

$$E=39 \times R2(1+0.045/R1) \times \lambda 2 \times \sqrt{A}$$

$$E=27 \times (1+R2/R1)^{1/3} \times (\lambda 2 \times R233 \sqrt{A})^{2/3}$$

$$E=2.3 \times (1+R2/R1)^{1/3} \times (R2 \times \delta \times \sqrt{A})^{2/3}$$

wherein R1 represents the distance (in m) between the X-ray source and the imaging object; R2 represents the distance (in m) between the imaging object and the X-ray image detector; λ represents the wavelength (in Å) of the maximum value of the X-ray dose; A (in mm) represents the diameter of the circle when the imaging object is assumed to be a column; and δ represents the difference in refraction between a substance and air.

The apparatus described in Japanese Patent Application No. 11-266605 is an X-ray image capturing apparatus which captures X-ray refraction contrast images. Said apparatus is equipped with an imaging object holding unit on the securing member, which is movable and temporarily fixable, as well as a film cassette holding unit; and it is possible to maintain the distance between a Coolidge X-ray tube and the screen-film system of said film cassette holding unit at at least 70 cm, and it is also possible to maintain the distance between said imaging object of the imaging object holding unit and the screen-film system of said film cassette holding unit at at least 20 cm.

Further, the method described in Japanese Patent Application No. 11-266605 is an X-ray image capturing method which captures X-ray refraction contrast images. In said method, equipped are with an imaging object holding unit on the securing member, which is movable and temporarily fixable, as well as a film cassette holding unit. It is possible to maintain the distance between a Coolidge X-ray tube and the screen-film system of said film cassette holding unit at at least 70 cm, and it is also possible to maintain the distance between said imaging object of the imaging object holding unit and the screen-film system of said film cassette holding unit at at least 20 cm.

The apparatus described in Japanese Patent Application No. 2000-53562 is an radiation image capturing apparatus which comprises a small focus radiation source which irradiates an imaging object, a holding member which secures said imaging object, reading means which reads radiation images formed by radiation transmitted through said imaging object, a distance varying means which varies a first distance between said small focus radiation source and said holding means, or a second distance between said holding means and said reading means, and a controlling means which controls the radiation conditions of said small focus radiation source. In said apparatus, said controlling means controls the radiation conditions of said small focus radiation source in accordance with the distance information regarding the first or second distance.

Further, said apparatus is a radiation image capturing apparatus which comprises a small focus radiation source which irradiates an imaging object, a holding means which secures said imaging object, reading means which reads radiation images formed by radiation transmitted through said imaging object, an image displaying means which displays radiation image information or an image output means which outputs radiation image information, and a control means which displays the radiation image information utilizing an image displaying means while being varied from an image magnification factor during radiation radiography or outputs said radiation image information utilizing said image outputting means.

The ordinary imaging as described herein refers to a radiography method in which an imaging object is brought into close contact with a detector and imaging is carried out, if desired, via a grid. The ordinary capture image as described herein refers to the image obtained utilizing said ordinary imaging.

Further, said radiation radiography apparatus in which phase contrast radiographic images can be obtained as direct digital images is one in which ordinary radiography (general radiography, which is ordinarily carried out) as well as phase contrast radiography can be carried out.

In the present invention, the embodiments are described with reference to the attached drawings. However, even though each drawing shows only one example, this embalmment is not limited to said example.

First, described are the embodiments of the phase contrast radiographic image processing apparatus, as well as the phase contrast radiographic image detection processing apparatus described in claims 1 through 32.

FIG. 1 is a view showing the constitution of the phase contrast radiographic image processing apparatus as well as the phase contrast radiographic image detection processing apparatus. The phase contrast radiographic image processing apparatus as well as the phase contrast radiographic image detection processing apparatus shown in the present embodiments comprises control section 10. Radiation generating source 30 is controlled by control section 10, but it is not limited to control utilizing said control section 10. Radiation from radiation generating source 30 transmits imaging object 5 and is irradiated onto radiography panel 41 which is provided in front of radiation image reading unit 40 as radiation image detecting means 200.

Employed as said radiation generating source 30 are Mo tubes, Rh tubes, W tubes, and the like. In the phase contrast radiographic imaging, a high-output X-ray source with the small focal spot size of a tube is preferred. As one example of methods to increase the X-ray output, a method is considered in which, during the irradiated of an electron beam, a rotating anode moves gradually so that said electron beam which is irradiated onto said rotating anode (a target) does not hit the same site on the concentric circle of said rotating anode. In order to capture phase contrast radiographic images, a radiation generating source preferably has a radiation tube focal spot size of from 30 to 500 µm and preferably generates a maximum tube electric current of at least 50 mA.

The preferred embodiments will now be described regarding the arrangement of said X-ray tube focus. In the radiography of an arm near a breast, when ordinary radiography is utilized, said imaging object is brought into close contact with a detector. As a result, it is possible to capture the image of the region placed on said detector irrespective of the position of said X-ray tube focus. Namely, when the breast image is captured, it is possible to capture the image including the walls of the chest. On the other hand, in the magnifying radiography such as phase contrast radiographic images, an imaging object is separated from said detector. As a result, when the position of said X-ray tube focal spot, as well as said detector with respect to said subject, is not appropriate, it is impossible to capture an acceptable image of the desired region. Namely it is necessary to optimize said X-ray tube focal spot or the arrangement of said detector.

Figure 2A:
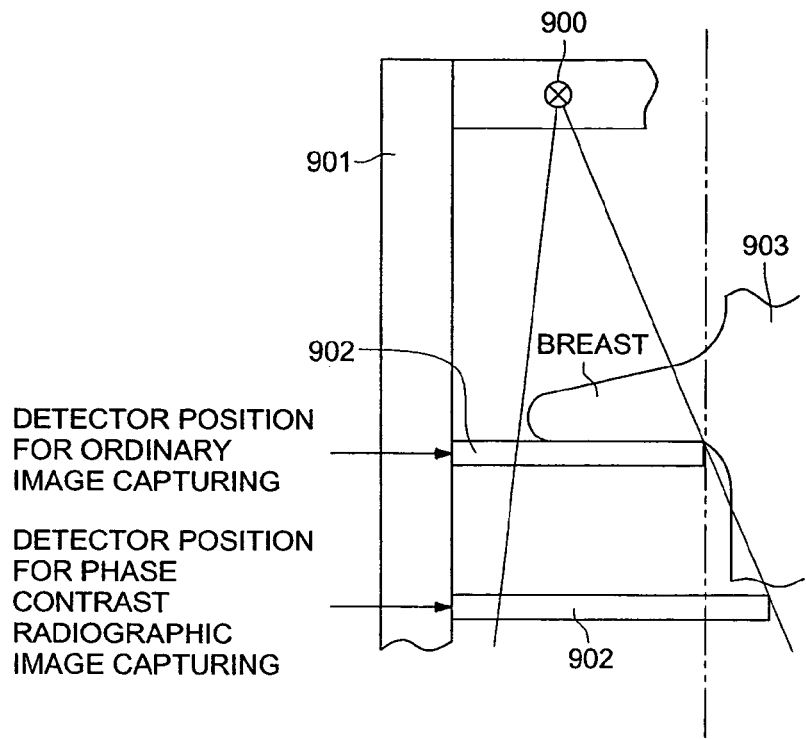
FIGS. 2(a) and 2(b) schematic views showing a breast imaging apparatus.

For instance, in a breast radiography apparatus, as illustrated in FIG. 2(a), X-ray tube focus 900 is arranged somewhat nearer column 901 (far from the imaging object) than the upward position perpendicular to the end of the imaging object holding section. In this case, in the magnifying radiography, such as phase contrast radiographic images, when it is desired to clearly capture the radiation information including the walls of the chest utilizing detector 902, problems occur in which it is difficult to capture the desired image since said detector 902 is positioned nearer the imaging object than the downward position perpendicular to the end of said imaging object holding section.

Figure 2B:
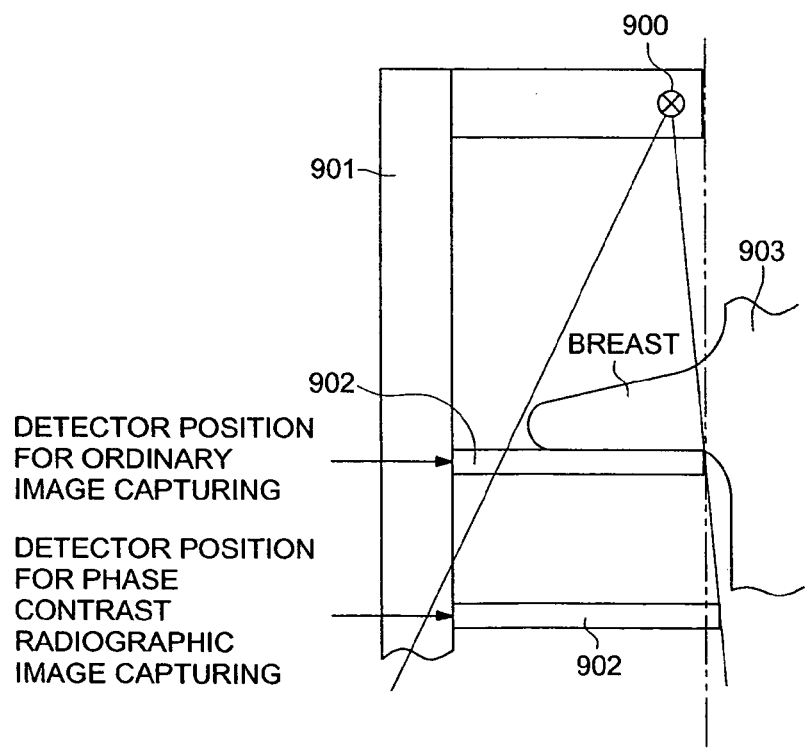

Due to that, as illustrated in FIG. 2(b), in the magnifying radiography such as phase contrast radiographic images, it is desired that said X-ray tube focus 900 is arranged nearer the side of subject 903 than that of the ordinary radiography.

Said arrangement of X-ray tube focus 900 is not limited to the radiography of digital phase contrast radiographic images, but is applied to analog systems such as screen/film, as well as ordinary magnifying radiography.

In radiation image reading unit 40, a detector is employed which makes it possible to obtain phase contrast radiographic images as direct digital data. Said detectors include those in which solid state image sensors such as a stimulable phosphor plate (imaging plate), flat panel detector, FPD (direct system and indirect system), and the like, and fluorescent materials ($Gd_2O_2S$: Tb, CsI, etc.), a lens (or a taper), and CCD, are employed, and the like. Since phase contrast radiographic images are formed utilizing magnifying radiography, the utilization of these detectors is equivalent to a decrease in the pixel size of said detector, and thus results in advantages of an increase in image information.

When radiation (X-rays, α-rays, β-rays, γ-rays, electron beam, ultraviolet rays, and the like) is irradiated onto said stimulable phosphor plate, some of said radiation energy is stored. Thereafter, exciting light, such as visible light, and the like) is irradiated, said plate generates stimulable radiation in accordance with stored energy. By employing such storage florescent materials (stimulable phosphors), the radiation image information of a human body, and the like, is recorded on a sheet comprised of said storage fluorescent materials. Subsequently, the resulting storage fluorescent material sheet is subjected to scanning employing exciting light such as a laser beam and the like so as to generate stimulable luminescence. The resulting stimulable luminescence is then photoelectrically read to obtain image signals. Based on the resulting image data, it is possible to output the radiation image of the imaging object onto recording materials, such as photosensitive photographic materials, CRTs, and the like, as visible images (refer to Japanese Patent Publication Open to Public Inspection Nos. 55-124929, 56-163472, 56-104645, 56-116340, and others).

As described, for example, in Japanese Patent Publication Open to Public Inspection No. 6-342098, solid state imaging devices such as flat panel detectors and the like, are comprised of a photoconductive layer which forms electrical charges corresponding to the intensity of irradiated X-rays, while utilizing a system in which formed charges are stored in a plurality of two-dimensionally arranged condensers. As described in Japanese Patent Publication Open to Public Inspection No. 9-90048, a system is employed in which X-rays are absorbed in a fluorescent material layer such as intensifying screens to illuminate fluorescence and the intensity of the resulting fluorescence is detected employing light detectors such as photodiodes and the like, which are provided with each pixel. Fluorescence detecting means include methods which employ CCD or C-MOS sensors other than these. Further, employed is a constitution in which X-ray scintillators, which emit visible light when irradiated with X-rays, lens arrays and region sensors corresponding to each lens, are combined.

Further, being different from the constitution shown in FIG. 1, for example, when in massive examination, the radiography of radiation images is performed usually employing X-ray film, a laser digitizer is employed in order to input the resulting radiographs into the system of the present embodiment. This is carried out in such a manner that each radiograph is subjected to scanning utilizing a laser beam and the amount of transmitted light is determined, and digital image data are obtained by applying analog digital conversion to the resulting data. By inputting said image data to control section 10, it is possible to treat them as the same digital data as those previously described.

When X-ray images are obtained utilizing the various aforementioned constitutions, the effective pixel size of the images is preferably no more than 200 μm, though this depends on radiography regions and diagnostic purposes, and is preferably no more than 100 μm, especially for mammogram. Further, the number of gradations of the images is preferably at least 10 bits, and is most preferably at least 12 bits.

In the phase contrast radiography, magnified radiography is essential. Therefore, a detector having a greater area is occasionally required. In such a case, as one of the application examples, there is a method in which radiography is carried out by arranging a plurality of image plates or screen/film; after the radiography, images are superimposed and the resulting images are subjected to processing. Further, a detector, in which many units comprised of the aforementioned fluorescent materials, lens, and CCD are arranged, is effective for an increase in the region. In these cases, it is required to interpolate jointed edges of images (gaps) employing appropriate interpolation processing processing.

In ordinary radiography, a grid is generally employed, though its use depends on the imaging region. However, in phase contrast radiography, since it is possible to remove scattered X-rays utilizing an air gap, said grid is not employed. Therefore, no absorption of radiation by said grid results in no loss of radiation information.

Control section 10 is connected with input means 27 such as a keyboard, and the like, via input interface 17. By operating said input means 27, input of management information regarding information for identifying obtained image data and radiography, and the like, is carried out.

Further, said control 10 is also connected with output means 28 via output interface 18. The preferred embodiments of said output 28 include those in which images are formed by processing silver halide light-sensitive photographic materials employing an automatic processor and the like, and images are obtained by heating other silver halide light-sensitive photographic materials in accordance with radiation image information. In addition, preferred embodiments are the use of hard copies prepared by an ink jet recording method in which images are made by ejecting ink from nozzles. Incidentally, the ink is solid at room temperature and is liquefied upon heating, while in another ink jet method, images are made by ejecting dyes or pigments, which are liquid at room temperature, from nozzles; a method in which images are made by heating an ink ribbon to sublimate dyes so as to adhere onto recording media; an ablation image forming method in which a sheet prepared by applying carbon and the like to one surface is heated employing a laser beam in accordance with image information so that said carbon is evaporated to form images, and the like.

Further, output means 28 ordinarily outputs, or displays, one image after processing. In addition, however, it is possible to output or display linearly arranged images before and after processing, or to output or display linearly arranged images when they are the images from the same imaging object.

Management information, showing information regarding the identification of imaging object 5 under image capturing, and imaging is inputted into control section 10, employing output means 27. The input of the management information, employing said input means 27, is carried out operating a keyboard or utilizing magnetic cards, bar codes, HIS (information system in a hospital: information management utilizing a network), and the like. Said management information is comprised, for example, of ID number, name, birth date, sex, imaging day and time, imaging region and imaging physical position (for example, the part of human body irradiated with radiation and the directing of the irradiated of said radiation), imaging method (simple imaging, contrast imaging, homographic imaging, magnification factor imaging, and the like), imaging conditions (tube voltage, tube current, irradiated time, distance R1 between the X-ray tube focus and the imaging object, distance R2 between the imaging object and the detector, magnification factor ratio, use or non-use of a scattered X-rays removing grid, identification of phase contrast radiographic images or normal imaging image, sampling pitch of the detector, diagnostic purpose and the like. However, items are not limited to those stated above.

Said control section 10 comprises CPU 11 as well as image processing means 100. It is possible to automatically obtain imaging date and time from CPU 11, utilizing a clock function such as calendar and time, built in said CPU 11. Furthermore, inputted management information may be limited to the imaging object to be imaged at that time or a series of management information may be inputted so that imaging objects are imaged in the inputted order or inputted management information is retrieved whenever it is necessary.

Control section 10 comprises image processing means 100 which applies image processing to phase contrast radiographic images as well as ordinarily captured images, and can apply image processing to image signals outputted from radiation image reading unit 40, which is radiation image detecting means 200 which outputs image signals corresponding to captured phase contrast radiographic image, as well as ordinarily captured images. Control section 10 can also apply image processing to image signals corresponding to phase contrast radiographic images as well as ordinarily captured images outputted from input means 27.

Image processing means 100 comprises phase contrast radiographic image processing means 110 which applies image processing to phase contrast radiographic images, as well as ordinarily captured image processing means 120 which applies image processing to ordinarily captured images. Since image processing conditions are different depending on either phase contrast radiographic images or ordinarily captured images, phase contrast radiographic image processing means 110 as well as ordinarily captured image processing 120 corresponding to each of them is provided.

Further, control section 10 comprises radiography information storing means 300 which stores management information regarding radiography. Image processing means 100 determines image processing conditions utilizing information regarding radiography stored in said radiography information storing means 300, and carries out processing based on the determined conditions.

Said management information, regarding radiography, may be stored in radiography information storing means 300 or may be stored in the images themselves as header information, and the like.

Figure 3:
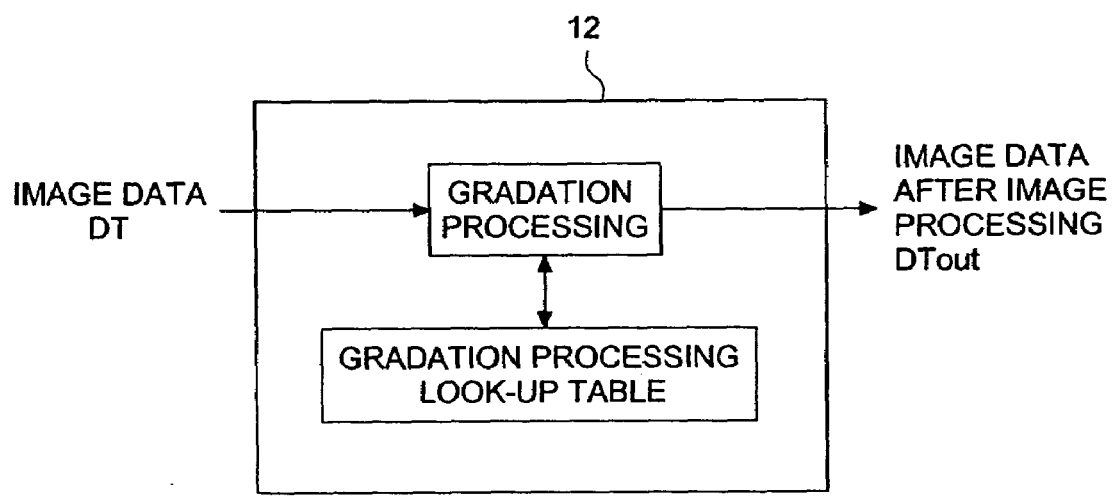
FIG. 3 is a diagram showing the constitution of an image processing path.

Phase contrast radiographic image processing means 110, as well as ordinarily captured image processing means 120, is comprised of image processing path 12 shown in FIG. 3. In said image processing path 12, even though the distribution of the image data level of phase contrast radiographic images or ordinarily captured images, gradation processing is carried out to obtain radiation images with density as well as contrast, suitable for diagnosis.

Further, even though not shown in FIG. 3, in said image processing path 12, carried out may be frequency enhancement processing which controls the sharpness of radiation images with respect to image data, DTreg, and dynamic range compression processing so that the entire radiation image having a broad dynamic range is included in the readily observable density range without need to decrease the contrast of fine structural part of an imaging object.

Incidentally, during the capture of radiation images, in order that radiation is not applied onto the part which is not required for diagnosis, or in order to minimize the decrease in resolution due to the incident radiation scattered in the unnecessary diagnostic part to the necessary diagnostic part, radiation non-transmitting materials, such as lead plate and the like, are provided with some part of imaging object 5 and radiation generating unit 30, and irradiated field narrowing, which limits the irradiated field of radiation to imaging object 5, is carried out.

When level conversion and gradation processing are carried out after that, employing image data in the interior of irradiated field narrowing field and in the exterior of the same, in the case in which said irradiated field narrowing is carried out, the image processing of the part required for diagnosis in the irradiated field is not properly carried out. Due to that, the irradiated field recognition to identify the interior region of the irradiated field and the exterior region of the same is carried out.

Figure 4:
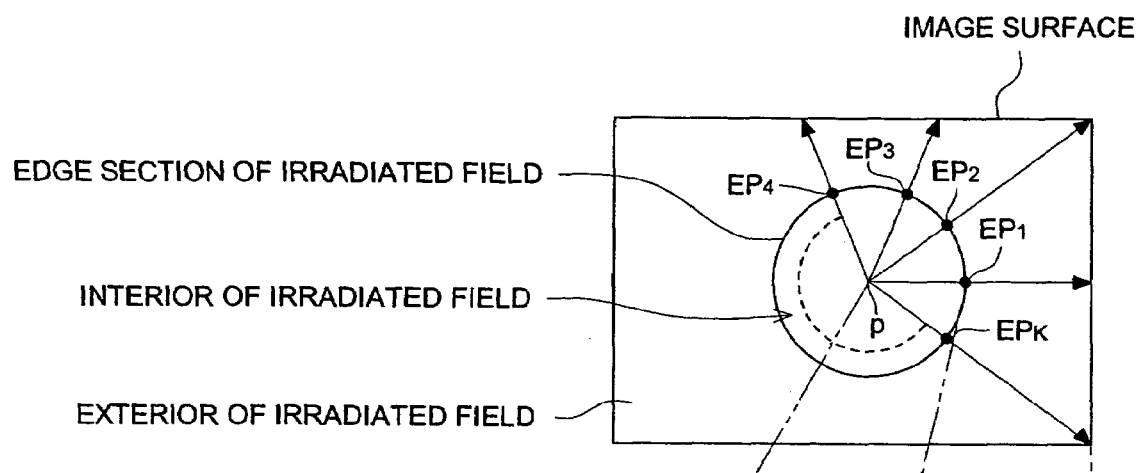
FIGS. 4(a) and 4(b) are views showing an irradiated field perceiving processing.
Figure 4:
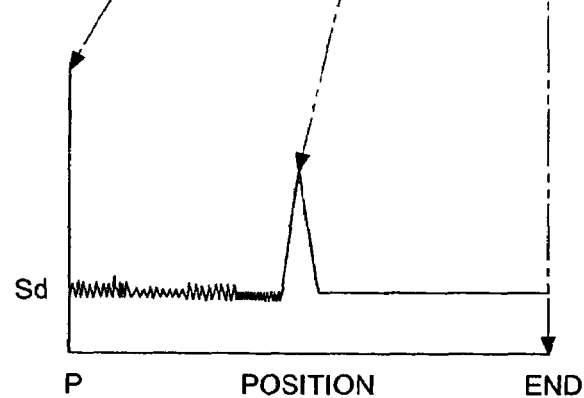

In said recognition of the irradiated field, for example, a method, which is described in Japanese Patent Publication Open to Public Inspection No. 63-259538, is employed. As shown in FIG. 4(A), for example, differentiation is carried out utilizing image data on the line directed from specified position P on an imaged surface to the edge of said imaged surface. Differential signal Sd, which is obtained by carrying out said differentiation, results in an increase in the signal level in the edge of the irradiated field. Thus irradiated field edge candidate point ET is obtained. By radiately carrying out a process to obtain said irradiated field edge points utilizing the specified point on the imaged surface as the center, a plurality of irradiated field edge candidate points EP1 to EPk are obtained. By connecting edge candidate points adjacent to a plurality of irradiated field edge candidate point EP1 to EPk, employing straight lines or curved lines, an irradiated field edge is obtained.

Further, it is possible to employ a method disclosed in Japanese Patent Publication Open to Public Inspection No. 5-7579. In said method, when an imaged surface is divided into a plurality of small regions, the amount of radiation approximately decreases uniformly in said small region in which the radiation is shielded by narrowing the irradiated field, and the dispersion value of image data decreases. Further, in the small region of the irradiated field, the amount of radiation is subjected to modulation. As a result, the dispersion value increases compared to that in the exterior of the irradiated field. Further, in a small region comprising the irradiated field edge, parts having the minimum amount of radiation exist together with parts having the amount of radiation modulated by the imaging object. As a result, the dispersion value is maximized. Based on these, small region comprising the irradiated field edge is identified based on the dispersion value.

Still further, it is possible to employ a method disclosed in Japanese Patent Publication Open to Public Inspection No. 7-181609. In said method, image data are moved by rotation utilizing a specified rotation center, and subsequently, by employing a parallel state detecting means, said rotation is carried out until the boundary line of an irradiated field becomes parallel to the coordinate axis of an orthogonal coordinate provided on the image. When said parallel state is detected, by utilizing a straight-line equation calculating means, the straight-line equation of the boundary prior to rotation is derived, employing the rotational angle and the distance from the rotation center to the boundary line. Thereafter, it is possible to identify the region of the irradiated field by determining the region surrounded by a plurality of boundary lines utilizing said straight-line equation. Further, when the irradiated field edge is a curved line, for example, one boundary point is extracted based on the image data, utilizing a boundary point extraction means and the next boundary point is successively extracted from boundary candidate points around said boundary point. In the same manner as above, the boundary point is successively extracted from boundary candidate points around said boundary point. Thus, it is possible to identify the region of the irradiated field, even though the irradiated field edge is a curved line.

When the irradiated field is identified as described above, the interior region of the identified irradiated field is provided as the region (hereinafter referred to as the region of interest) which is employed to determine the level distribution of image data during converting the distribution of image data to the distribution of the desired level. A representative value is determined from the image data in said region of interest, and it is possible to obtain the image data of the desired level by converting said representative value to the desired level.

Said region of interest is not limited to the case in which said region is equal to the interior region of the irradiated field. For example, it is ordinarily carried out that upon performing diagnosis, the most important part is positioned as the center of the irradiated field. Accordingly, it may be designated as the region of interest by proving a circular or rectangular region positioned at the center of the interior region of the irradiated field. Herein, said circular or rectangular region is provided in such a manner that the diameter of the circle or the length of line of the rectangle is, for example, in the range of from "½" to "⅕" of the long side or short side or diagonal line of the irradiated field.

Furthermore, said region of interest corresponding to the specified human anatomy may be provided in the interior region of the irradiated field. For example, as described in Japanese Patent Publication Open to Public Inspection No. 3-218578, projection (cumulative value of image data in one direction) in the longitudinal direction and the transverse direction is obtained, and by employing an anatomical region determining means, the region of a lung field is determined based on the resulting data so that the determined region is set as the region of interest. Further, as disclosed in Japanese Patent Publication Open to Public Inspection No. 5-7578, image data of each pixel are compared to the threshold value, and based on the comparison results, an identification symbol is added to each pixel. Subsequently, labeling is carried out for every pixel group having continuous symbols showing at least the threshold value, and thereby a region is determined. The determined region is then set as the region of interest. Subsequently, from the image data in the region of interest, representative values D1 and D2 are set, and conversion of said representative values to desired levels S1 and S2 is carried out. Further, a region (hereinafter referred to as the "signal region"), which is employed to set a representative value from the region of interest, is extracted, and representative values D1 and D2 are set from the image data in the extracted signal region.

Figure 5A:
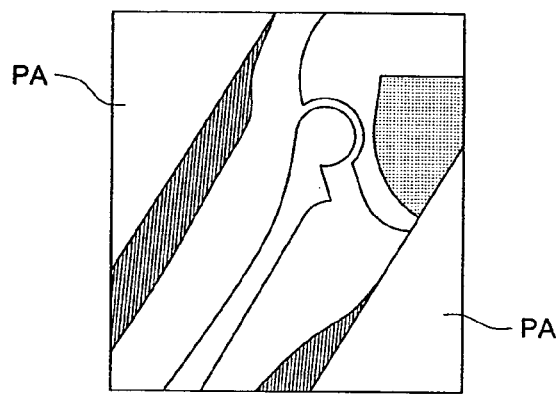
FIGS. 5(a) to 5(c) are views showing the extraction method of a signal region.
Figure 5B:
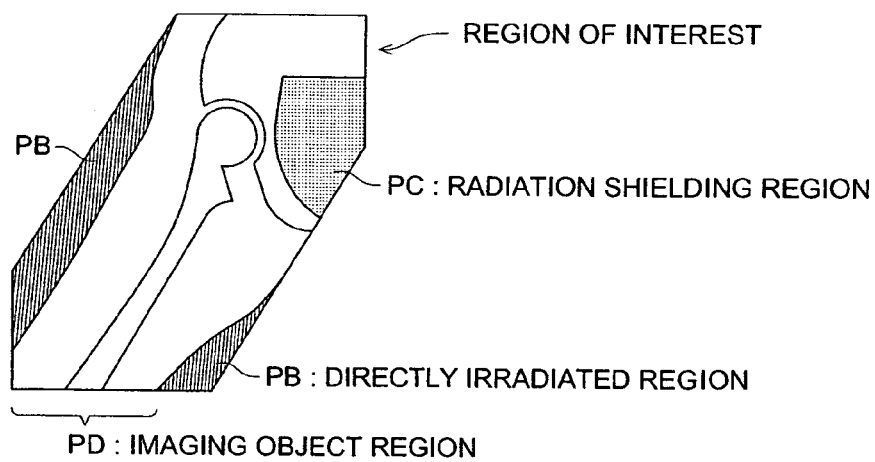
Figure 5C:
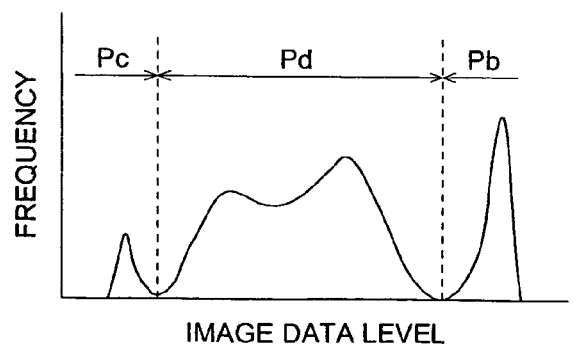

A method to extract said signal region from the region of interest is such that a histogram of image data is prepared, and the signal region is extracted based on said histogram. For example, FIG. 5(A) shows a part of the coax of a human body, and region PA is one which is not irradiated due to the narrowing of the irradiated field. FIG. 5(B) is a view in which the irradiated field is identified and the region in the identified irradiated field is set as the region of interest. FIG. 5(C) shows the histogram of the image in said region of interest. Directly irradiated region PB in the region of interest, shown in FIG. 5(B), is a region in which radiation is not transmitted through an imaging object, but is directly irradiated. Thus the radiation amount is large. Due to that, as shown in FIG. 5(C), said directly irradiated region PB corresponds to region Pb having the high level of image data. Further, radiation shielded region PC (a region in which radiation is shielded utilizing radiation protection units, and the like) in the region of interest, is irradiated with a small amount of radiation due to the shielding. Due to that, said radiation shielded region PC corresponds to region Pc having a low level of image data. Further, in imaging object region PD in the region of interest, radiation is modulated by the imaging object, and said imaging object region PD corresponds to region Pd between region Pb having a high level of image data and region Pc having a low level of the same. As described above, it is possible to identify the imaging object region utilizing said histogram of image data. Thus region Pd is identified as the signal region while removing region Pb, having a high level of image data as well as region Pc having a low level of the same shown in FIG. 5(C).

Further, in the extraction of the signal region, it is possible to employ a method disclosed in Japanese Patent Publication Open to Public Inspection No. 63-262141. In this method, the histogram of image data is divided into a plurality of small regions, utilizing an automatic threshold value selection method, employing a discrimination standard method and the like, and the desired image region among the divided small regions is extracted as the signal region.

In the setting of representative values D1 and D2, for example, an approximate minimum value, as well as an approximate maximum value, in the region of interest and the extracted signal region are employed as the representative values. Further, signal values, in which the cumulative histogram in the signal region shows specified values, e.g. 20 percent and 80 percent, are employed as representative signal values. Further, employed as one of the representative values is a signal value, for example, in which the cumulative histogram in the signal region reaches 60 percent. In setting representative values D1 and D2, by utilizing the image data in the signal region, it is possible to carry out processing which is more suitable for the imaging object than the case in which image data in the region of interest is employed.

As described above, a region of interest setting means, which sets a desired region of interest upon analyzing phase contrast radiographic images, is comprised of and based on the image signal in the set region of interest, image processing conditions are determined. Based on the determined conditions, processing is carried out. Since processing conditions are determined based on the image signals in the region of interest, it is possible to determine optimal processing conditions.

Incidentally, said region of interest setting means makes it possible to carry out the following. By analyzing ordinarily captured images in the same manner, the desired region of interest is set, and based on the image signals in the set region of interest, image processing conditions are determined. Subsequently, it is possible to carry out based on the determined conditions.

Figure 6:
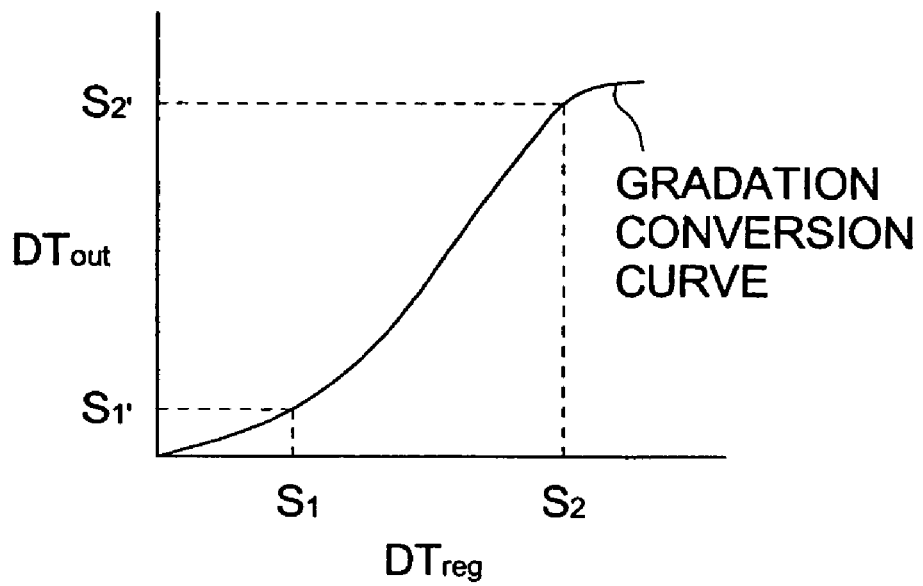
FIG. 6 is a graph showing gradation conversion characteristics.

Subsequently, as shown in FIG. 3, gradation processing is carried out employing image data DTreg. In said gradation processing, for example, a gradation conversion curve, as shown in FIG. 6, is employed. Image data DTreg are converted to output image data DTout, utilizing standard values S1 and S2 of image data DTreg as S1' and S2'. Said S1' and S2' correspond to specified luminance or photographic density of the output images.

Said gradation conversion curve is preferably represented by a continuous function over the entire image signal region of image data DTreg. Further, the resulting differential function is preferably continuous. In addition, the sign of the resulting differential coefficient is preferably not varied over the entire signal region.

Further, the shape of preferred gradation conversion curve as well as levels S1' and S2' vary depending on the imaging region, the imaging physical position, imaging conditions, imaging methods, and the like. Accordingly, said gradation conversion curve may be prepared for each image when needed. Further, as shown in Japanese Patent Publication No. 5-26138, a plurality of basic gradation conversion curves is previously stored and the desired gradation conversion curve may be readily obtained by retrieving any of said basic gradation conversion curves and by rotating or moving the basic curve in parallel. Further, as shown in FIG. 3, in image processing path 12, a gradation processing lookup table, which corresponds to a plurality of basic gradation conversion curves, is provided. Image data, obtained by referring to said gradation processing lookup table based on image data DTleg, is subjected to correction in accordance with the rotation and parallel movement of said basic gradation conversion curve so that image data DTout, which have been subjected gradation conversion, can be obtained. Further, in said gradation conversion, two standard values S1 and S2 are not only employed, but also one standard value or at least three standard values may be employed.

Herein, the selection of said basic gradation conversion curve and the rotation as well as the parallel movement of the selected basic gradation conversion curve are carried out based on the imaging region, the physical imaging position, the imaging conditions, the imaging method, and the like. When information regarding these is inputted as the management information, utilizing input means 27, it is possible to readily select the basic gradation conversion curve, utilizing said management information. Further, the level of standard values S1 and S2 may be varied based on the imaging region, the physical imaging position, the imaging conditions, and the imaging method.

Further, the selection of said basic gradation conversion curve and the rotation as well as the parallel movement of the selected basic gradation conversion curve may be carried out based on information regarding types of image display apparatus, as well as types of peripherals for image output. This is due to the case in which preferred gradation varies depending on the image output system.

Employed as methods other than those described above are those described in Japanese Patent Publication Open to Public Inspection Nos. 55-116339, 55-116340, 57-66480, 59-83149, 63-31641, 63-262141, 2-272529, 3-2185785-75925, 5-174141, 5-344423, 6-233755, 7-255012, 7-271972, 8-62751, 8-331385, 9-261471, 9-266901, 10-32756, 10-63831, 11-88688, 11-316832, 2000-23950, 2000-30046, 2000-33082, 2000-79110, and others. Naturally, gradation conversion methods are not limited to those above, and other various methods may be employed. Further, regarding the shapes of gradation conversion curves, for example, those disclosed in Japanese Patent Publication No. 63-20535 may also be employed.

As described above, the gradation processing conditions vary depending on either phase contrast radiographic images or non-phase contrast radiographic images as well as information other than that. Therefore, image processing means 100 comprises a gradation processing means which carries out gradation conversion.

Further, said gradation processing comprises a gradation conversion curve storing means which stores a plurality of gradation conversion curves. In said gradation processing means, one gradation conversion curve is selected from a plurality of gradation conversion curves which are stored in said gradation conversion curve storing means, and gradation conversion is carried out based on the selected gradation conversion curve.

In said gradation processing means, one gradation conversion curve is selected from a plurality of gradation conversion curves stored in said gradation conversion curve storing means.

Further, said gradation processing comprises a basic gradation conversion curve storing means which stores a plurality of basic gradation conversion curves, and in said gradation processing means, one basic gradation conversion curve is selected from a plurality of basic gradation conversion curves stored in said basic gradation conversion curve storing means. Processing is then carried out in which the desired gradation conversion curve is prepared by modifying the selected basic gradation conversion curve, and based on the prepared gradation conversion curve, gradation conversion is carried out.

In said gradation processing means, a basic gradation conversion curve is selected from a plurality of basic gradation conversion curves stored in said basic gradation conversion curve storing means, based on management information regarding radiography.

In said gradation processing means, processing is carried out under the conditions in which a contrast coefficient with respect to phase contrast radiographic images is smaller than that with respect to ordinarily captured images. The contrast coefficient as described herein refers to a gradient of between two optional points of a characteristic curve in which the abscissa represents the logarithm of the X-ray irradiated amount and the ordinate represents the signal value of the detector. Further, as another definition of said contrast coefficient, it refers to a gradient of a line drawn by connecting a point reaching a density of "fog density+0.25" with a point reaching a density of "fog density+2.0" in said characteristic curve. When radiation images are phase contrast radiographic images, the image contrast of phase contrast radiographic images is set to be higher than that of ordinarily captured images. Accordingly, the contrast coefficient in the gradation processing is purposely set to be small so that images results in excellent graininess.

Frequency enhancement processing as well as dynamics range compression processing will now be described.

Image processing means 100 comprises a frequency enhancement processing means which carries out frequency enhancement processing. In said frequency enhancement processing, since sharpness is controlled employing unsharp masking, for example, shown in Formula (1), function F is determined utilizing methods disclosed in Japanese Patent Publication Nos. 62-62373 and 62-6237.

$$Soua = Sorg + F(Sorg - Sus) \tag{1}$$

wherein Soua represents image data after processing, Sorg is image data prior to frequency enhancement processing, and Sus represents unsharp data which are obtained by applying averaging processing to image data prior to frequency enhancement processing.

Figure 7:
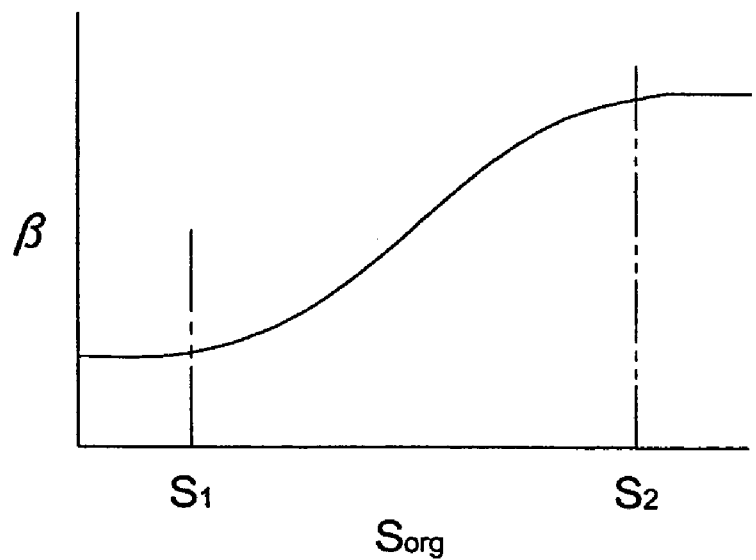
FIG. 7 is a graph showing the relationship between the enhancement coefficient and the image data.

In said frequency enhancement processing, for example, F(Sorg−Sus) is modified to β×(Sorg−Sus), and as shown in FIG. 7, β (enhancement coefficient) almost linearly varies between standard values S1 and S2.

Figure 8:
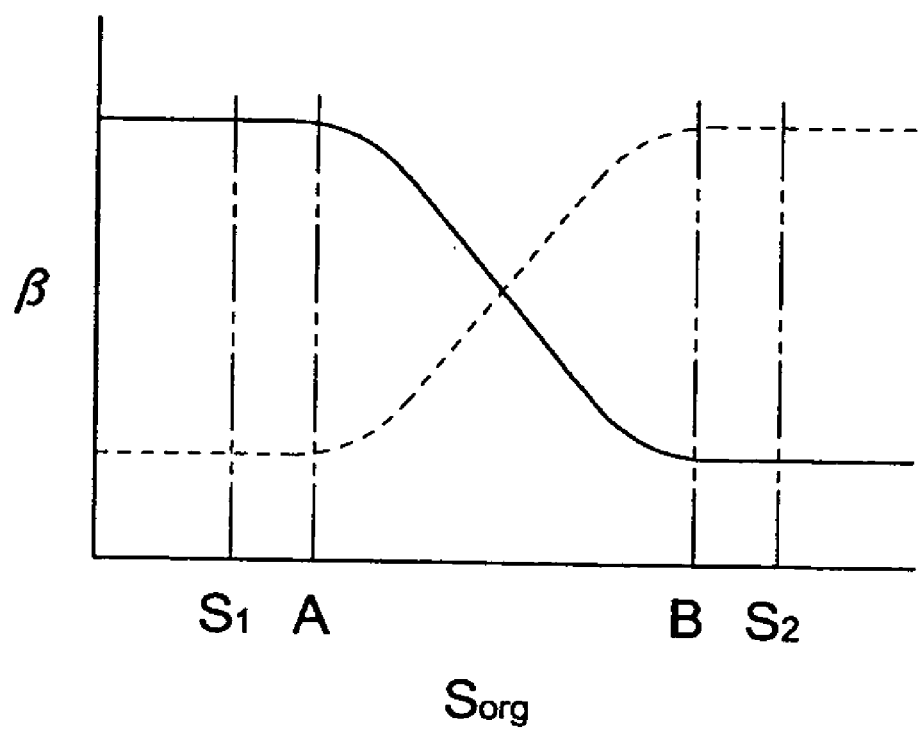
FIG. 8 is a graph showing the relationship between the enhancement coefficient and the image data.

Further, as shown by the solid line in FIG. 8, when low luminance is enhanced, β between standard value S1 and value "A" is maximized while β between value "B" and standard value S2 is minimized. Further, β between values "A" and "B" varies almost linearly. Further, even though not shown, intermediate luminance is enhanced so that β between values "A" and "B" is maximized. As described above, in the frequency enhancement processing, it is possible to control the sharpness of the luminance part utilizing function F.

Herein, standard values S1 and S2, and values A and B are obtained employing the same determining method as that which is employed to determine standard values S1 and S2 during the setting of the frequency enhancement processing conditions previously described. Further, said frequency enhancement processing method is not limited to the aforementioned unsharpness mask processing, but other methods may also be employed such as those described in Japanese Patent Publication Open to Public Inspection Nos. 55-87953, 55-163472, 56-104645, 5-174141, 5-252444, 6-233755, 6-235982, 7-21364, 7-51257, 7-160876, 10-63812, and 2000-4398; Japanese Patent Application Nos. 4-048825, 7-42277, 7-73433, 7-73497, 7-94693, and 7-316679; Japanese Patent Publication Nos. 62-62373, 62-62376, and 62-62379; and others. Further, a multiple definition method (described in Japanese Patent Publication Open to Public Inspection Nos. 5-244508, 6-301766, and 9-44645) may be employed. Naturally, frequency enhancement processing methods are not limited to these, but various other methods may be employed as well.

Further, in said frequency enhancement processing, frequency enhancement processing conditions are determined utilizing the management information regarding radiography, and said processing may be carried out based on the determined conditions.

Incidentally, in said frequency enhancement processing, the enhanced frequency range and the degree of enhancement are set based on the imaging region, imaging conditions, imaging methods, and the like, in the same manner as the selection of basic gradation conversion curves, and the like, in the gradation processing.

In said frequency enhancement processing, the degree of enhancement of phase contrast radiographic images is less than the frequency enhancement coefficient of ordinarily captured images. The degree of enhancement as described herein refers to coefficient β in Formula (1). When radiation images are phase contrast radiographic images, said phase contrast radiographic images are comprised of more high-frequency components than ordinarily captured images. Accordingly, the frequency enhancement coefficient in the frequency enhancement processing is reduced. As a result, it is possible to decrease high-frequency component noise.

Further, image processing means 100 comprises a dynamic range compression processing means which carries out dynamic range compression processing. In said dynamic range compression processing, compression processing, illustrated by Formula (2), is carried out, and the resulting density range is controlled so as to be more easily visualized. Accordingly, function G is determined utilizing a method disclosed in Japanese Patent Publication No. 266318.

$$Stb = Sorg + G(Sus) \tag{2}$$

wherein Stb represents image data after processing, Sorg represents image data prior to dynamic range compression processing, and Sus represents unsharp data obtained by averaging image data prior to dynamic range compression processing, and the like.

Figure 9A:
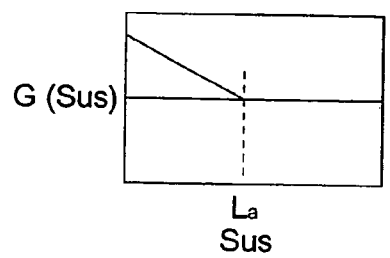
FIGS. 9(a) to 9(e) are series of graphs explaining dynamic range compression processing.
Figure 9D:
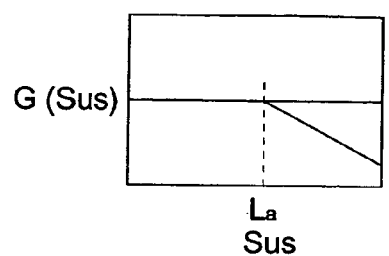
Figure 9B:
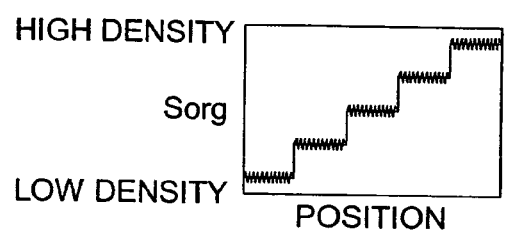
Figure 9E:
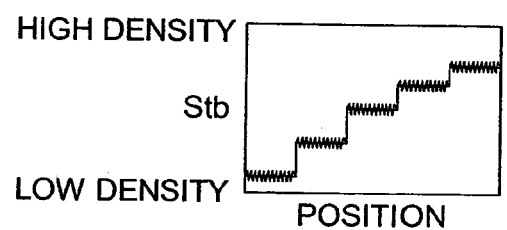
Figure 9C:
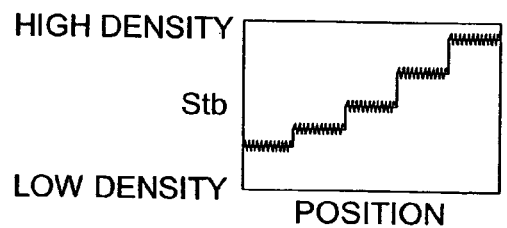

Herein, as shown in FIG. 9(A), when unsharp data Sus exhibit such characteristics that when it becomes less than level "La", G(Sus) increases, the density in the lower density region is regarded to be high, and image data Sorg shown in FIG. 9(B) are regarded as image data Stb which are subjected to dynamic range compression in the lower density region as shown in FIG. 8(C). Further, as shown in FIG. 9(D), when G(Sus) exhibits such characteristics that when unsharp data Sus become less than level "Lb", G(Sus) decreases, the density in the higher density region is regarded to be high and image data Sorg, shown in FIG. 9(B), are subjected to dynamic range compression in the higher density region as shown in FIG. 9(E). Herein, levels "La" and "Lb" are obtained employing the same determining method employed to determine standard values S1 and S2 during the setting of the aforementioned gradation processing conditions.

Further, in said dynamic range compression processing, the correction frequency band as well as the degree of its correction is set up based on the physical imaging position, the imaging conditions, the imaging methods, and the like.

As described above, said embodiments make it possible to always obtain consistent radiation images with regard to density, as well as contrast, suitable for diagnosis, and the like, by applying said gradation processing to obtained image data, and at the same time, to obtain radiation images within the more easily visualized density range without the degradation of the contrast of fine structure part of imaging objects, employing said dynamic range compression processing.

As described above, in said dynamic range compression processing, the degree of correction for phase contrast radiographic images is greater compared to the coefficient for ordinarily captured images.

In Formula (2), it is possible to express function G of FIG. 9(A), for example, as described below:

$$G=\beta \cdot (La-Sus)$$

when $\beta$ is a constant, $Sus \leq La$, when $\beta$ is 0, $Sus > La$.

The degree of correction as described herein refers to coefficient $\beta$ of Formula (2). The larger degree of correction as descried herein means that $\beta$ is larger or La is larger.

When radiation images are phase contrast radiographic images, the sharpness of phase contrast radiographic images is better than ordinarily captured images. Accordingly, even though said coefficient during the dynamic range compression processing is set to be larger, it is possible to minimize the decrease in sharpness.

Employed as methods of said dynamic range compression methods other than those described above may be those described in Japanese Patent Publication Open to Public Inspection Nos. 63-189043, 63-189854, 3-222577, 5-174141, 5-300376, 6-121795, 6-292008, 6-292009, 6-292013, 6-339025, 7-38758, 8-294006, 9-266901, 11-41541, 11-191150, 11-101150, and others. Naturally, the methods are not limited to these, and it is possible to apply various other gradation conversion methods.

Further, in said dynamic range compression processing, dynamic range compression processing conditions are determined based on management information regarding radiography, and said processing may be carried out under said determined conditions.

The embodiments of the phase contrast radiographic image processing apparatus described in claims 33 through 39 will now be described.

First, be described will be energy subtraction. One imaging object is subjected to irradiation of radiation having different energy distribution levels. By utilizing the fact that the specified anatomical part (for example, internal organs, bones, blood vessels, and the like) exhibits characteristic absorption of the radiation energy, two image signals, in which said specified anatomical part is differently imaged, are obtained. Thereafter, two signals are subjected to pertinent weighting and subtraction between two signals to extract said specified anatomical part.

The example of the specific method of said energy subtraction is as follows. Two sheets of a detector are subjected to single shot energy subtraction which simultaneously records radiation images, each of which holds a high energy component and a low energy component, and image signals holding the radiation image of an imaging object are obtained from each detector. By carrying out subtraction processing between each signal, an image, in which the specified structure portion of said imaging object is enhanced, is obtained. Further, single shot is not always required and a plurality of shots may be acceptable.

Figure 10:
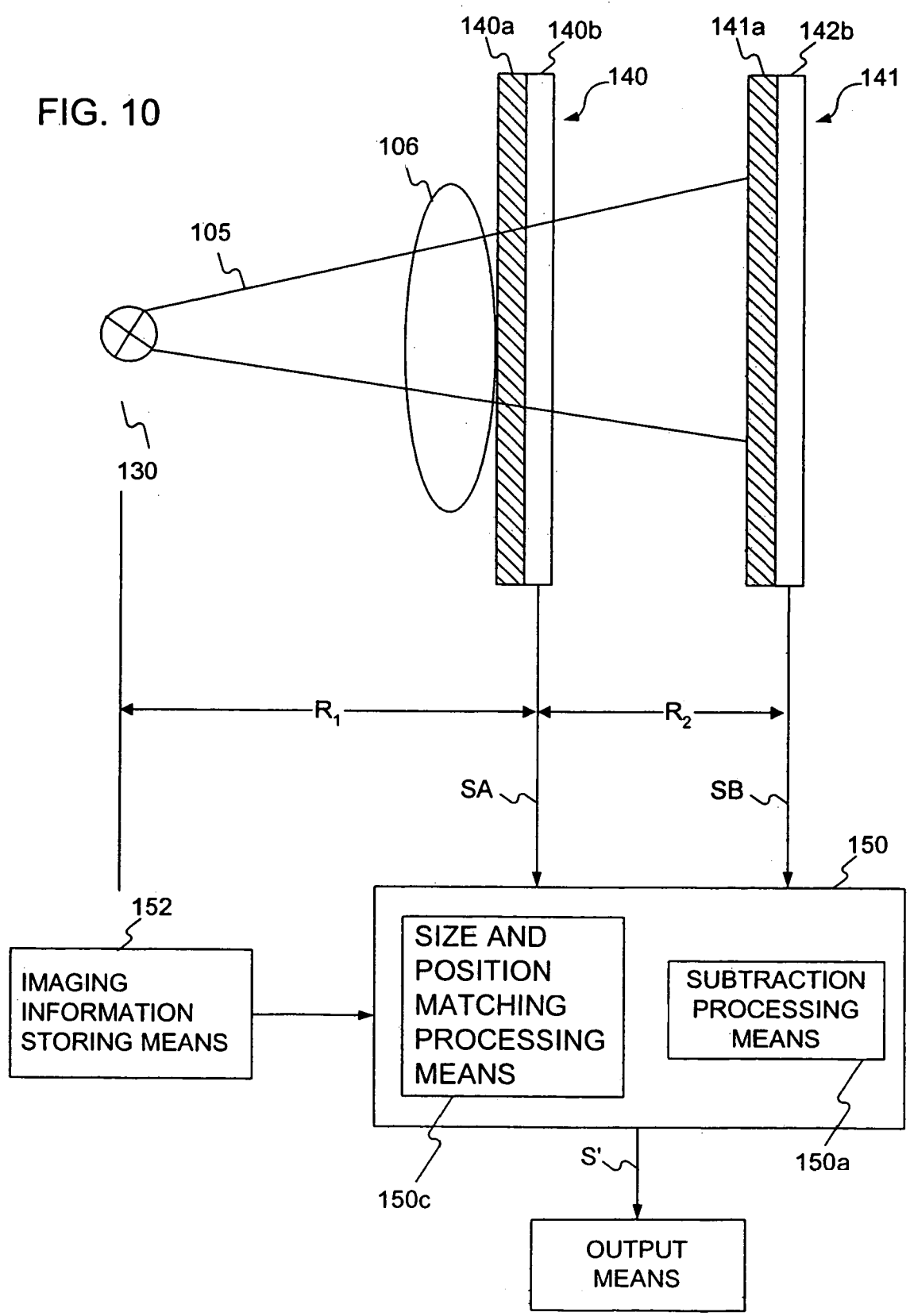
FIG. 10 is a view showing another embodiment of a phase contrast radiographic image processing apparatus.

FIG. 10 is a view showing the constitution of a phase contrast radiographic image processing apparatus. The phase contrast radiographic image processing apparatus in this embodiment comprises a radiation image reading unit having a detector constituting units 140 and 141. Said detector constituting units 140 and 141 are comprised of flat plate-shaped scintillators 140a, solid light detector 140b laminated to each of 140b, and 141b.

Radiation 105 emitted from radiation generating source 130 is irradiated onto imaging object 106 and transmitted through said imaging object 106. Radiation 105, which is transmitted through said imaging object 106, is irradiated onto detector constituting unit 140 of said radiation image reading unit. Radiation 105, which is irradiated onto said detector constituting unit 140, is first irradiated onto scintillator 140a.

Said scintillator 140a emits visible light of an intensity corresponding to the intensity of irradiated radiation 105, and the resulting visible light is received by solid light detector 140b. Subsequently, said visible light is subjected to photoelectric conversion, and signal electrical charge is stored in solid light detector 140b in response to the emission intensity. Thereafter, said signal charge is read from a conveyance section, and image signal SA is outputted as the electric signal. Said image signal SA becomes the image signal of ordinarily captured images.

On the other hand, radiation 105, irradiated onto detector constituting unit 140, which is not converted by said scintillator 140a, is transmitted through solid light detector 140b; reaches detector constituting unit 141; and is converted to visible light utilizing scintillator 142a; and is received by solid light detector 141b. Subsequently, said visible light is subjected to photoelectric conversion, and a signal charge is stored in solid light detector 141b in response to emission intensity. Thereafter, said signal charge is read from solid light detector 141b, and image signal SB is outputted as the electric signal. Said image signal SB becomes the image signal of ordinarily captured images.

In this embodiment, a plurality of radiation images are captured by a single X-ray irradiation and from these images, subtraction images are obtained. Behind the imaging object, a plurality of detectors is arranged so that a plurality of images is simultaneously obtained by a single X-ray irradiation. Since a plurality of radiation images has the same image shape, there is no discrepancy in the shape when position matching.

Figure 11:
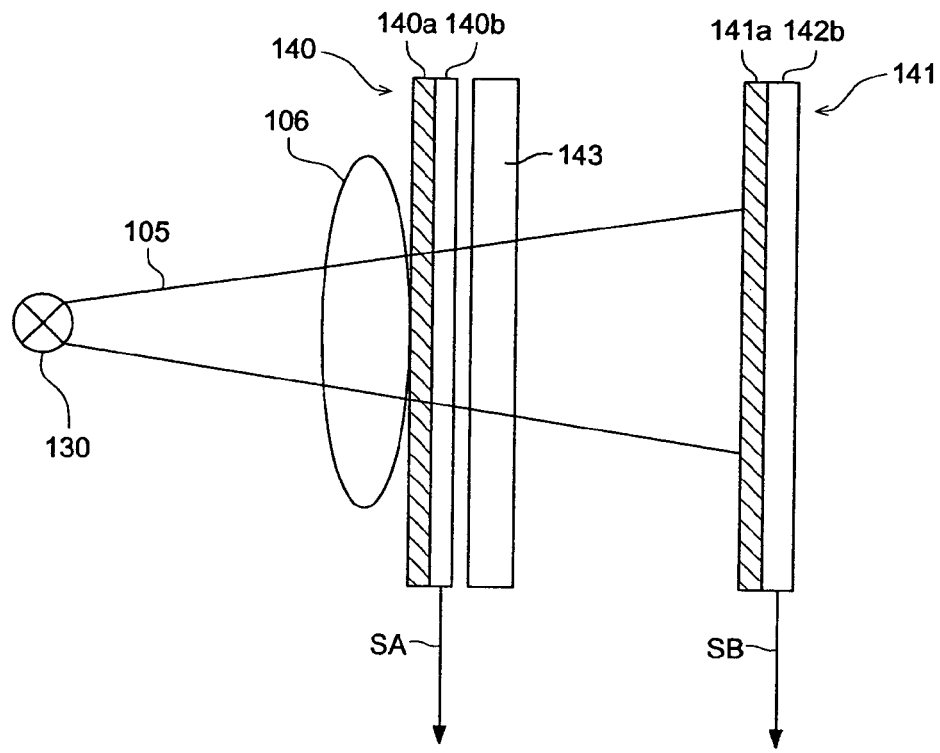
FIG. 11 is a view showing the constitution of another embodiment of a radiation image reading unit.

Further, as shown in FIG. 11, it is possible to place filter 143 comprising materials which absorb the low energy component of radiation at at least one site between detector constituting units 140 and 141 each of which are detectors of a radiation image reading unit.

Specifically, it is preferable that said filter be arranged immediately behind solid light detector 140b of detector constituting unit 140. Since filter 143 comprises materials which absorb low energy components of X-rays, X-rays, which are transmitted through said filter 143, are subjected to a decrease in the low energy components and thus are such a state so as to have a relatively large high energy component. Due to that, detector constituting unit 141 receives information in which image information, related to the low energy component of X-rays is less compared to detector constituting unit 140.

On the other hand, instead of said filter 143, a detector, which exhibits different enegy absorption characteristics, may be employed. In that case, a detector, which exhibits high absorption characteristics of the low energy components, is employed at the position nearer to the radiation generating source 130.

Said outputted image signals SA and SB are inputted to control section 150, are subjected to weighting, and are then subjected to difference. Namely, $$S=k1 \cdot SA+k2 \cdot SB \tag{3}$$

wherein k1 and k2 each represent a weighting coefficient. Employing k1 and k2, calculation is performed, and image signal S is obtained (since S is the difference, herein, either k1 or k2 is a negative value). Furthermore, image processing and the like is carried out with respect to said image signal S. Processed image signal S is inputted, for example, to output means 151 and the radiation image of imaging object 106 is outputted as a visible image.

A weighting means is preferably comprised which carries out specified weighting with respect to a plurality of radiation images obtained as above. Each image is subjected to weighting so that the difference can be carried out while retaining the necessary portion. Namely, when two sheets of images exhibiting the preferred embodiment are employed, it is possible to obtain the specified difference image by carrying out the subtraction processing between SA, which is the signal of an ordinarily captured image, and SB, which is the signal of the phase contrast radiographic image.

Control section 10 comprises size and position matching means 150c which matches the sizes as well as the positions of a plurality of images. Since the sizes of phase contrast radiographic images are different from those of ordinarily capture images, it is required to accurately match the sizes as well as the positions of employed images. Due to the variation of sizes, corresponding pixels vary. In order to match the corresponding pixels, it is required to apply interpolation processing.

Said control section 10 comprises radiography information storing means which stores management information regarding radiography. When said management information regarding radiography comprises a magnification factor, the sizes of a plurality of images are matched based on the information of said magnification factor and optional interpolation processing, and thereafter, position matching is carried out.

Position matching methods include a method of parallel movement and template-matching, a method in which markers are simultaneously imaged, and the position is matched by matching the position of said markers, and the like.

Figure 12:
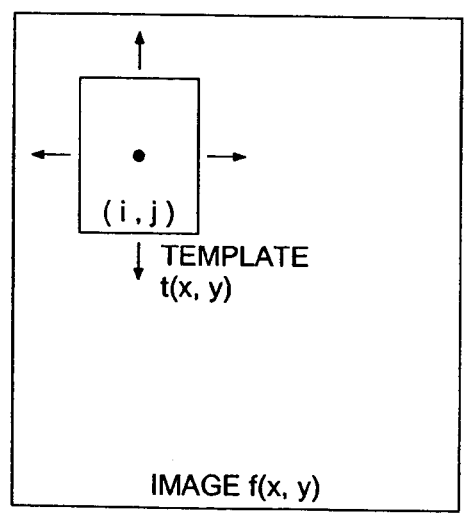
FIG. 12 is a view explaining template-matching.

Said template-matching method will now be described. As shown in FIG. 12, the center of template (x, y) representing a subject to be detected is managed so as to overlap point (i, j) in image f(x, y), and the degree of similarity between t(x, y) with the partial pattern of the image, which is overlapped with said image, is determined. The determined value is then regarded as certainty of the existence of said subject at point (i, j) (refer to "Computer Gazoshori Nyumon" (Introduction to Computer Image Processing)), page 149, published by Soken Shuppan Co., Ltd.).

Employed as methods in which markers are simultaneously imaged, and the position is matched by matching the position of said markers, can be those described in Japanese Patent Publication Open to Public Inspection Nos. 6-22219 and 10-108073.

Figure 13:
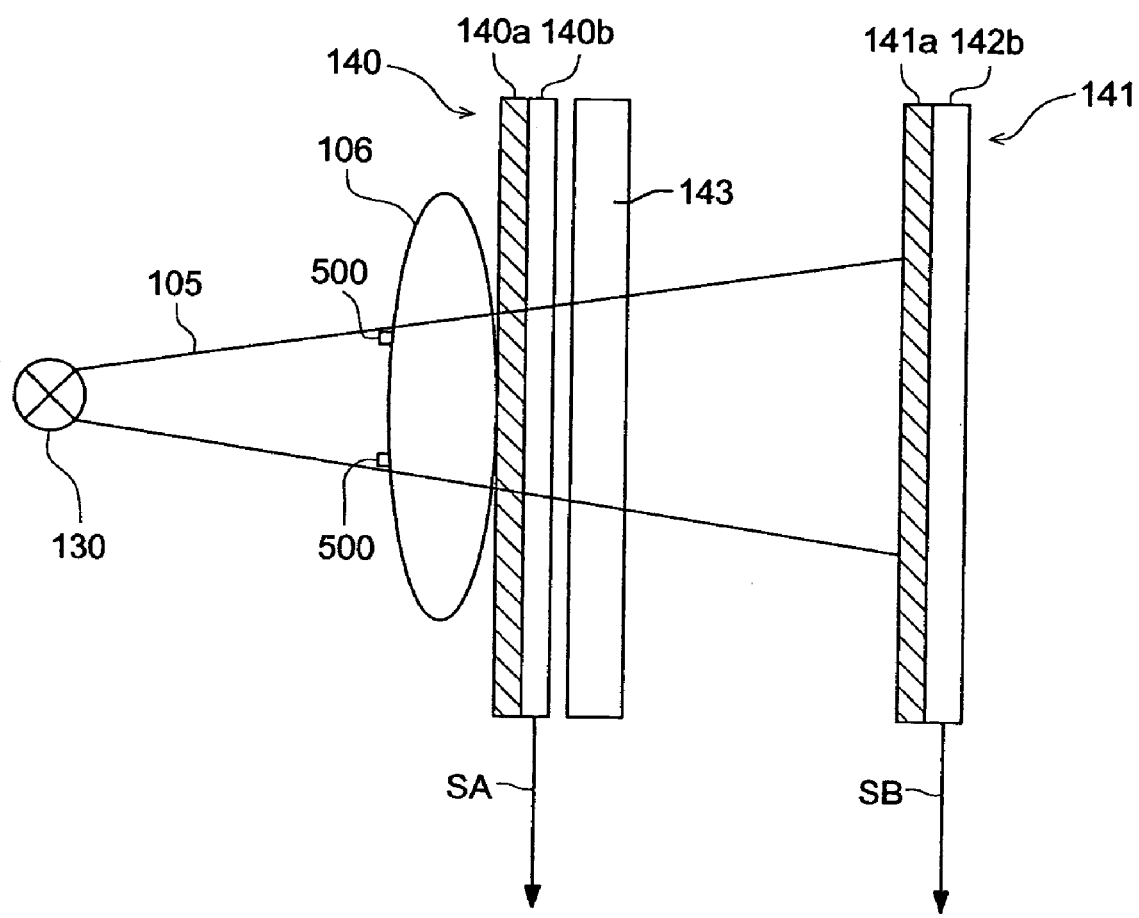
FIG. 13 is a view explaining position matching by positioning each of two X-rays under linear and rotational movements so that two markers are positioned at the same site.

In the method described in Japanese Patent Publication Open to Public Inspection No. 6-22219, the relative position matching of each X-ray image, which is held by two image signals SO1' and SO2', is carried out in terms of said image signals (refer to Japanese Patent Publication Open to Public Inspection No. 58-163338) and said position matching is carried out carried out utilizing relatively linear and rotational movement of two X-ray images so that two markers 500, shown in FIG. 13, are overlapped.

In the method described in Japanese Patent Publication Open to Public Inspection No. 10-108073, as position matching processing, it is possible to apply various methods known in the art such that in the case of capturing subject images, when specified markers for image matching are imaged, processing is carried out so as to match said markers, and such position matching processing utilizing two-dimensional non-linear image modification shown in Medical Imaging Technology, Vol. 11. No. 3, 1993, pages 373 to 374, and the like.

Further, the present embodiment comprises radiography information storing means 152 which stores management information regarding radiography. When a magnification factor is not included in management information regarding radiography, said magnification factor is obtained based on the analysis results, and the sizes of a plurality of images are matched, utilizing the obtained magnification factor, as well as optional interpolation processing, followed by position matching processing.

Analysis methods to obtain said magnification factor include one in which a plurality of markers or the distance of some part or the total of an imaging object is obtained, and said magnification factor is obtained based on the ratio of said distances. In this case, either manual or automatic, or both may be employed. Further, even though said magnification factor is not known, when R1 and R2 are included in the management information, it is possible to obtain the magnification factor utilizing the formula of magnification factor=1+R2/R1.

Control section 150 comprises subtraction processing means 150a which carries out subtraction processing of a plurality of radiation images, comprising at least one phase contrast radiographic image and obtains subtraction images. A plurality of detector sheets are subjected to a single shot energy subtraction which records (simultaneously) radiation images which holds each of high energy component and a low energy component of radiation, and the image signal which holds the radiation images of the imaging object is obtained from each detector. It is then possible to obtain images in which the specified structural portion is enhanced by carrying out subtraction processing between each of the signals.

Since phase contrast radiographic images are markedly excellent in the extraction capability of blood vessels and the like, for example, it is possible to extract regions such as blood vessels and the like utilizing the difference with ordinarily captured images. As a result, it is possible to capture images such as blood vessels and the like without employing contrast media.

In the present embodiment, it is preferable that difference images are prepared utilizing two images, in which one image is prepared by ordinary radiography and the other is prepared by phase contrast radiography.

Further, in the present embodiment, since the image quality of the ordinarily captured images is different from the phase contrast radiographic images, namely, in the phase contrast radiographic images, contours of blood vessels and the like are clearly imaged, it is unnecessary to prepare a detector which exhibits specifically different characteristics, and a detector having the same energy absorption characteristics may be employed. Naturally, such detector, which exhibits different energy absorption characteristics, may be employed, and X-ray energy may be subjected to conversion.

The preferred specifications of said phase contrast radiographic image processing apparatus is such that the imaging object holding unit, namely a human body, is not moved, but the detector, as well as the radiation source, is moved. When a distance is set in such a manner that a human body is not moved while the detector is moved, a person to be imaged will not feel uncomfortable. It is preferable that two detectors, one for ordinary radiography and the other for phase contrast radiography are incorporated in such a manner that the detector for the phase contrast radiography is positioned separate from the position of the imaging object holding unit at a definite distance and is movable.

Further, in the aforementioned example, a radiation image reading unit, comprised of a combination of a scintillator and a solid light detector, is employed. However, said example is not limited to this, and it is possible to utilize various types of radiation image reading units which were previously described.

Further, in the aforementioned radiation image reading unit according to the present invention, the filter, which absorbs the low energy component of radiation, is arranged between each of detector constituting units. However, it may be arranged at any position between the scintillators of each detector constituting unit.

Further, in the aforementioned example, it is employed to the radiating image of an imaging object by detecting the radiation irradiated through said imaging object. However, said example is not limited to this. For example, it is possible to apply so-called autoradiography in which the radiation image of an imaging object to be examined is obtained by detecting the radiation emitted from said imaging object itself.

The embodiments of the phase contrast radiographic image processing apparatus described in claims 40 through 45 will now be described.

Figure 14:
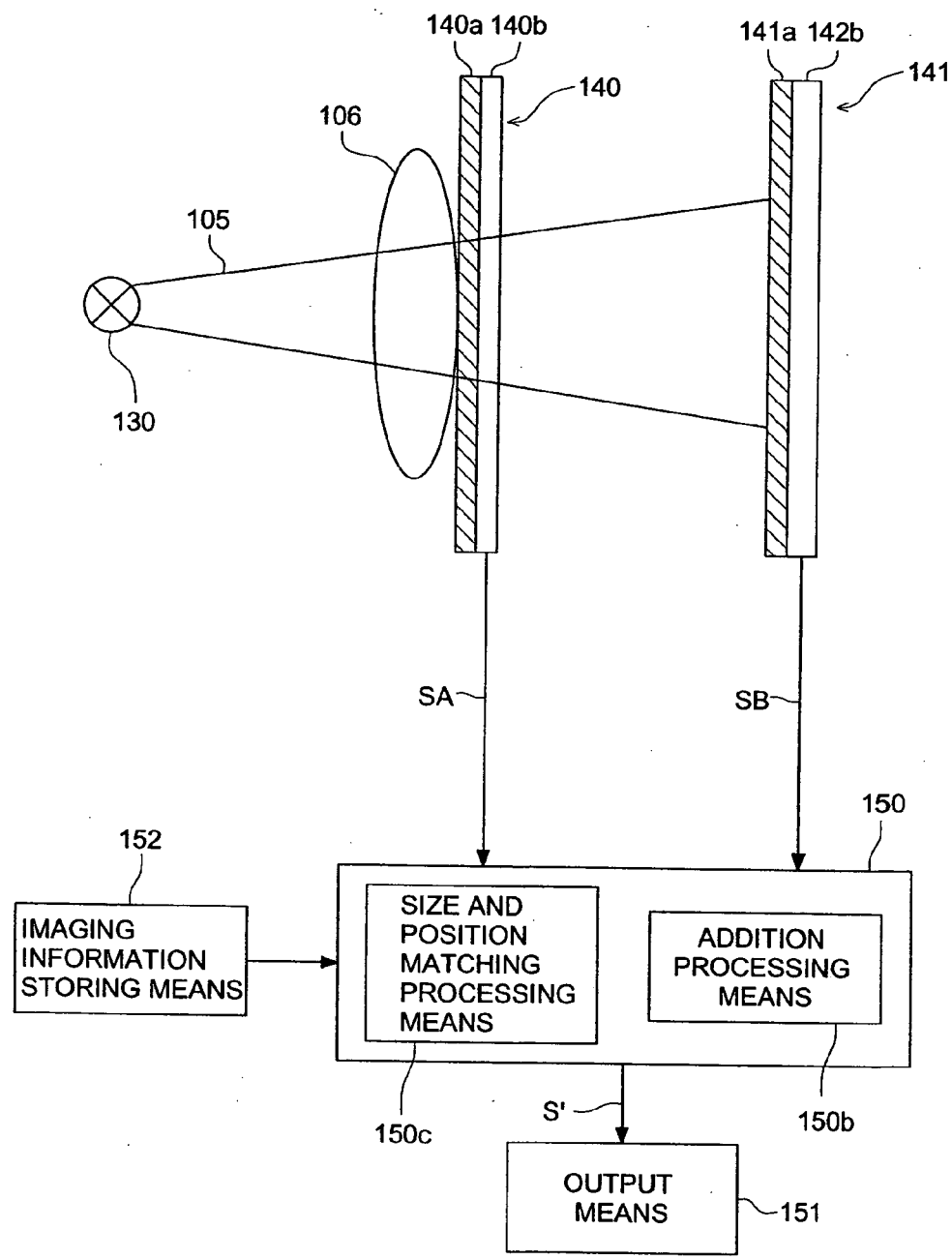
FIG. 14 is a view showing the constitution of another embodiment of a phase contrast radiographic image processing apparatus.

FIG. 14 is a view showing the constitution of a phase contrast radiographic image processing apparatus. The phase contrast radiographic image processing apparatus in said embodiment is constituted in the same manner as the embodiment shown in FIG. 10. However, subtraction processing means 150a in the embodiment shown in FIG. 10 is replaced with addition processing means 150b which obtains addition images in such a manner that addition processing is applied to a plurality of radiation images comprising at least one phase contrast radiographic image which is obtained by imaging the same subject employing control section 150. phase contrast radiographic images exhibit high sharpness and by applying said addition to said images, it is possible to obtain images with minimal noise and excellent graininess.

In this embodiment, a plurality of radiation images is imaged employing a single X-rays irradiation and addition images are obtained from said images. A plurality of detectors is arranged behind an imaging object so that a plurality of images is simultaneously obtained by a single X-ray irradiation. Since a plurality of said images has the identical shape, no shape deviation occurs during image position matching.

A weighting means is provided, which carries out the specified weighting with respect to a plurality of the obtained images, and each image is subjected to weighting in accordance with the aforementioned Formula (3).

Further, size and position matching means 150c, which matches sizes and positions of a plurality of images, is provided. Since the sizes of phase contrast radiographic images are different from those of ordinarily captured images, it is necessary to accurately match sizes as well as positions of the employed images. Corresponding pixels vary due to the variation of sizes. In order to match up the corresponding pixels, it is necessary to carry out interpolation processing.

Radiography information storing means 152 is provided, which stores management information regarding radiography. When magnification factors are included in the management information regarding radiography, sizes of a plurality of images are matched utilizing the information of said magnification factors as well as optional interpolation processing, and thereafter, position matching processing is carried out.

Said position and size matching is carried out employing the same methods as above.

Further, said phase contrast radiographic image processing apparatus may be provided with both subtraction processing means 150a in this embodiment shown in FIG. 10, and addition processing means 150b in the embodiment shown in FIG. 14. If desired, a plurality of radiation images comprising at least one phase contrast radiographic image obtained by capturing the same imaging object 106 may be subjected to subtraction processing, so as to result in subtraction images, while a plurality of radiation images may be subjected to addition processing, so as to result in addition images.

The embodiments of the phase contrast radiographic image output apparatus described in claims 46 through 51 will now be described.

Figure 15:
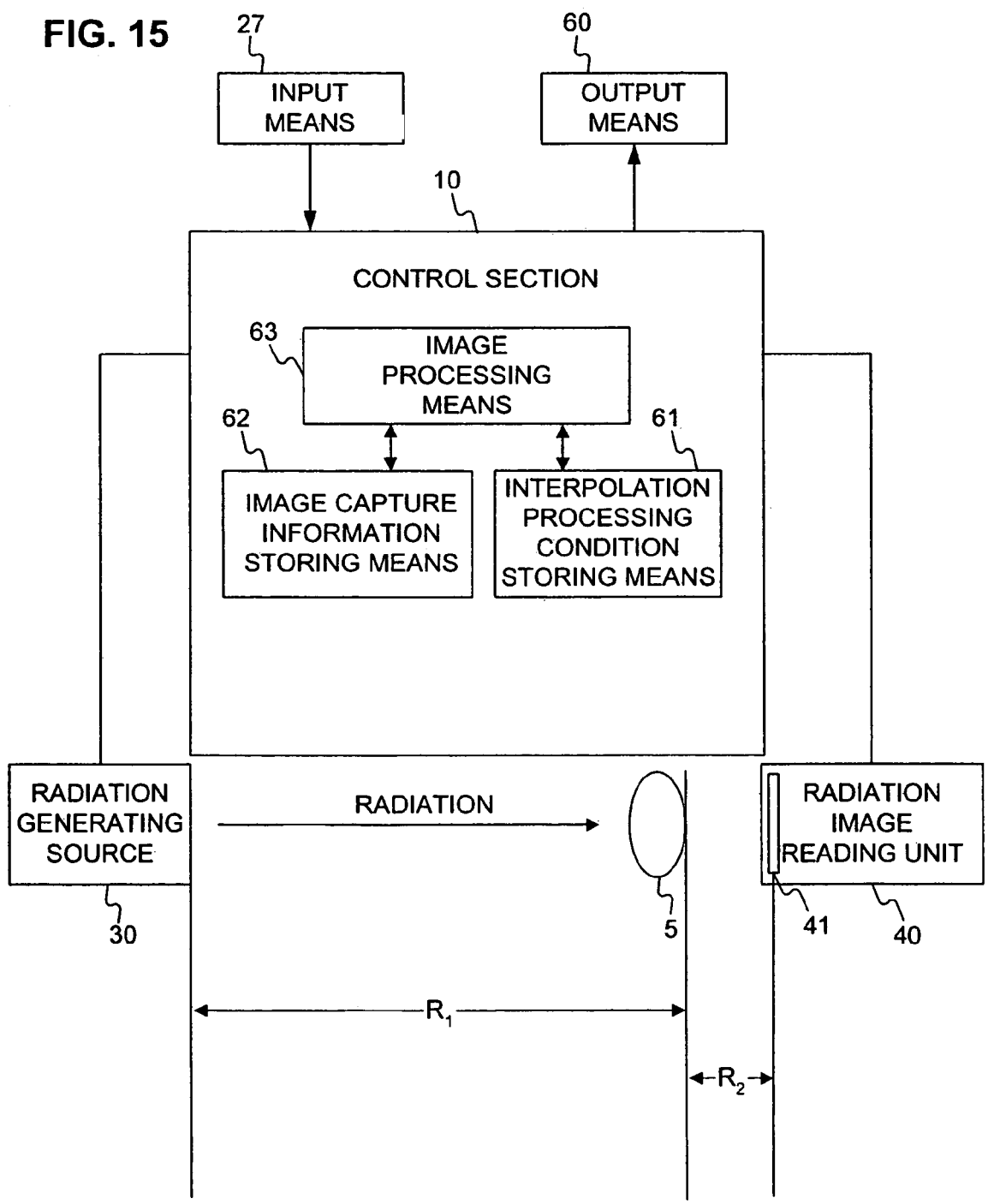
FIG. 15 is a diagram showing the constitution of still another embodiment of a phase contrast radiographic image processing apparatus.

FIG. 15 shows a phase contrast radiographic image output apparatus in this embodiment. The phase contrast radiographic image output apparatus in said embodiment is constituted in the same manner as the embodiment shown in FIG. 1. However, output means 60 is provided which outputs magnified phase contrast radiographic images under reduction factor $\alpha$ of no more than 1. Reduction factor $\alpha$ as described herein refers to a reduction factor which reduces captured images to the same sizes as the imaging object, that is, the inverse number of the magnification factor of captured images. Since phase contrast radiographic images are subjected to magnified imaging, captured images are larger than the imaging object. However, since sizes, which are ordinarily employed for diagnosis, are preferred, phase contrast radiographic images are preferably outputted under reduction. Specifically, the images are preferably outputted so as to be the same size as the imaging object. Even though the reduction factor for image output is set utilizing defaults, needless to say, it is possible to alter them as desired by users, since they are digital images.

After carrying out pertinent image processing via control section 10, it is possible to obtain hard copies, employing, for example, image output apparatus such as a laser imager, and the like, which are output means 60. At the same time, the preferred embodiment is such that, for example, by transmitting image data from said control section 10 to said laser imager, images are outputted while being automatically reduced to the specified size.

Further, employed as output means may be ones which are the same as those described in the embodiments of the phase contrast radiographic image processing apparatus, as well as the phase contrast radiographic image detection processing apparatus, described in the aforementioned claims 1 through 32.

Further, the phase contrast radiographic image output apparatus in said embodiment comprises interpolation processing condition storing means 61 which stores a plurality of the interpolation processing conditions. In output means 60, any of interpolation processing conditions are selected from a plurality of interpolation processing conditions which are stored in interpolation processing condition storing means 61 and the interpolation processing is carried out utilizing the selected interpolation processing conditions and radiation images are outputted.

Said interpolation processing is at least one which is selected from nearest neighbor interpolation processing, straight-line interpolation processing, spline interpolation processing, cubic-convolution interpolation processing, and bell-spline interpolation processing.

Further, radiography information storing means 62 is provided which stores management information regarding radiography. Interpolation processing conditions are determined based on said management information regarding radiography, and it is possible to carry out interpolation processing based on the determined conditions. For example, based on the information of magnification factor A of captured images, when images are outputted under the same size of the imaging object, images are outputted at a magnification factor of 1/A. By having said management information regarding radiography, optimal processing conditions are determined based on said management information regarding radiography, and processing is then carried so that images suitable for diagnosis can be obtained. For example, utilizing the information of R1 and R2, it is possible to obtain magnification factor M employing the formula of M=1+R2/R1, and images are reduced at a factor of 1/M and then outputted. Specifically, the method described below and the like is considered. When images are reduced at a factor of ½ and then outputted, employing a sampling pitch of 100 μm of said input apparatus, image sampling pitch is reduced to 50 μm (=100 μm×½) and output is then carried out employing any of several ordinarily employed methods.

Further, in said embodiment, it is preferable that interpolation processing be carried out based on the sampling pitch of input means 27, the sampling pitch of output means 60, and the magnification factor of captured images, and the imaged imaging objects are outputted at the same size as the imaged objects.

The sizes of outputted images, which are most suitable for diagnosis, are the same size as the imaging objects. As previously described, the size of one pixel is determined by dividing the sampling pitch of input means 26 by the magnification factor of images. The resulting size is compared to the sampling pitch of output means 60, and if desired, interpolation processing is carried out, and final images are outputted.

Image processing means 63 is provided, which prepares image data which are outputted from output means 60, utilizing the sampling pitch of input means 27, the sampling pitch of output means 60, magnification factors (reduction factors) of outputted images to inputted images, interpolation processing conditions, and the like. Said image processing means 63 may be in the interior of said control section 10, and a processing means may be included in said output means 60.

Further, of said management information regarding radiography, specified information is outputted while being attached to outputted images. Attached information such as magnification factors of captured images, reduction factors which are the inverse number of magnification factors, and the like, is useful during diagnosis.

Image output, as described in the aforementioned claims 46 through 51 means that images are printed out onto sheets of film or paper, and the like, but does not mean that images are displayed on CRT, and the like.

The sampling pitch as described herein refers to the space between pixels and is ordinarily the same as the pixel size.

When an image is outputted onto a plurality of sheets, there is a method in which an image having the same size as the imaging object and partially magnified image are displayed in a row. In this case, when the magnified part is displayed as an image having the same size as the imaging object, such images will be more easily comprehended. Image outputting methods include a method to output one image having the same size as the imaging object, a method to output one image having the same size as the imaging object, one partially magnified image in a row, and the like.

Separately from the methods as above, display methods onto CRT and the like include a method to output one image having the same size as the imaging object, a method to output one image having the same size as the imaging object, and partially magnified images in a row, and the like. When CRT is employed, after displaying a default image, it is possible for an operator to optionally vary and observe images.

The embodiments of the phase contrast radiographic image diagnostic supporting apparatus described in claims 52 and 53 will now be described.

For example, when doctors carry out image diagnosis employing radiation images, image reading has been carried out in such a manner that X-ray images are displayed on image display apparatus such as CRT and the like. Specifically, in recent years, techniques have been developed in which, by the use of digital image processing technique utilizing a computer, image data is analyzed, and abnormal shadow due to lung cancer, breast cancer, and the like are detected. It has become possible that information of abnormal shadow candidates is presented to doctors so that they can use the information to support their diagnosis.

Figure 16:
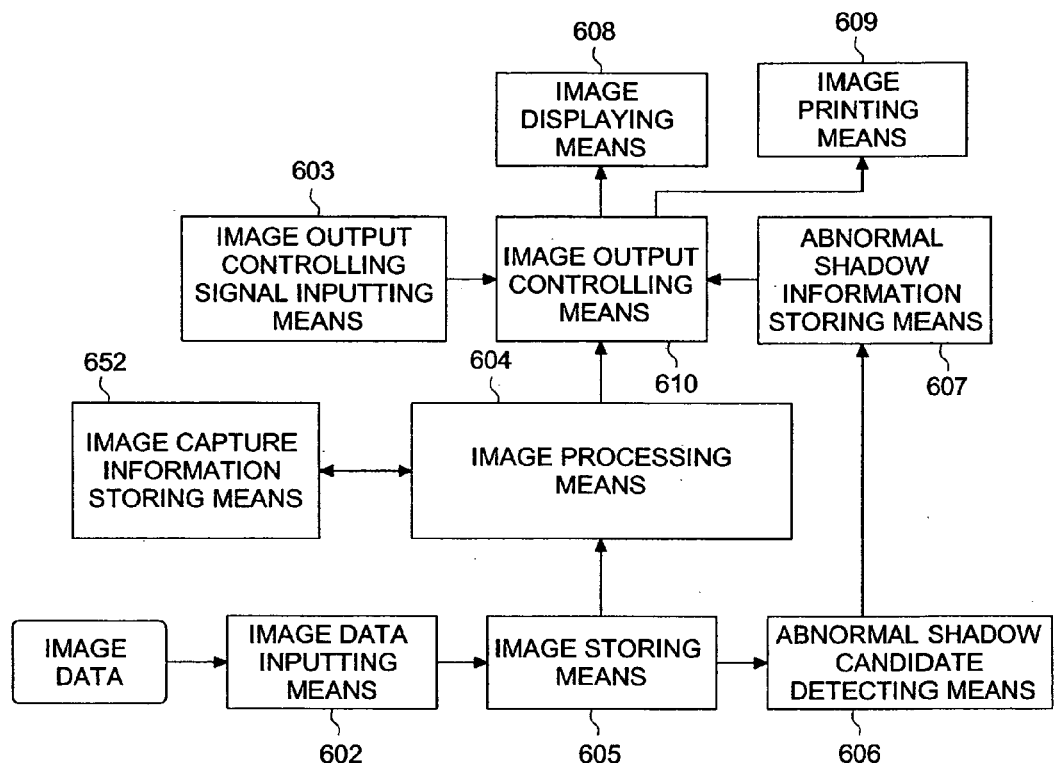
FIG. 16 is a schematic diagram showing an image diagnosis supporting apparatus.

The embodiment of such an image diagnosis supporting apparatus is shown in FIG. 16. The phase contrast radiographic image diagnosis supporting apparatus having said embodiment comprises image data inputting means 602, image output controlling signal inputting means 603, image processing means 604, image storing means 605, abnormal shadow candidate detecting means 606, abnormal shadow storing means 607, image output controlling means 610, image displaying means 608, and image printing means 609. Said image processing means 604 is connected to image information storing means 652.

Image data input from image data inputting means 602 is carried out in such a manner that, for example, in a group examination, radiation images are captured usually employing X-ray film. In order to input the resulting X-ray photographs to the system of said embodiment, a laser digitizer is employed. Said laser digitizer scans over the film utilizing a laser beam and the amount of the transmitted laser beams is determined. The obtained value is subjected to A/D conversion to be inputted as digital image data.

For inputting images, it is possible to employ apparatus utilizing photo-sensors such as CCD and the like. Instead of reading images on film, it is possible to connect an imaging apparatus which can directly output digital images utilizing cumulative phosphors as described in Japanese Patent Publication Open to Public Inspection No. 55-12429.

Further, it is possible to input X-ray images which are obtained employing a flat panel detector (FPD) which captures X-ray images utilizing a plurality of two-dimensionally arranged detecting elements and outputs captured images as electrical signals. These detectors will not be described herein because they were detailed previously.

When digital X-ray images are obtained employing the aforementioned various types of constitutions, for mammograms, for example, the effective pixel size of the image is preferably no more than 200 μm, and is more preferably no more than 100 μm, though this size depends on captured regions as well as diagnostic purposes. In order to allow the image diagnosis supporting apparatus of the present invention to exhibit its best performance, a preferred constitution is such that, for example, image data, which have been inputted employing effective pixel size of about 50 μm, are stored and displayed. In the abnormal shadow candidate detecting means, it is unnecessary to make the pixel size of the image data which are employed for the analysis of the abnormal shadow candidate detection equal to the pixel size of the inputted image. For example, the effective pixel size of the inputted image is set at 50 μm, and employed as image data employed for the abnormal shadow candidate detection may be those which are obtained in such a manner that the inputted image is subjected to thinned-out treatment and then to conversion so as to have an effective pixel size of 100 μm.

Inputted data, which, if desired, are subjected to data compression, are stored in image storing means 605. Herein, data compression is carried out employing reversible compression, or irreversible compression, utilizing methods known in the art such as JPEG, DPCM, Wavelet compression, and the like. Said reversible compression is preferred since the degradation of diagnostic information, along with data compression, is minimized.

In small-scaled diagnosis, since the amount of data is not so great, it is possible to store image data on magnetic disks without compression. In this case, it is possible to store and read image data at a very high speed compared to photomagnetic disks. Since during reading the shadow of images, a high speed cycle time is required, necessary image data are occasionally stored in a semiconductor memory.

Images stored in image storing means 605 are successively read out, are subjected to image processing employing image processing means 604, and are simultaneously subjected to detection for abnormal shadow candidates employing abnormal shadow candidate detecting means 606.

Said abnormal shadow candidate detecting means 606 analyzes image data which have been read out from said image storing means 605 and detects, for example, microcalcification clusters and tumor shadows, as shown in FIG. 17. FIG. 17(*a*) shows an example of said microcalcification clusters. The presence of the gathering of microcalcifications (cluster forming) indicates high possibility of the early stages of cancer. Therefore, said presence is one of the important observations to detect the early stages of breast cancer. On the mammogram, it is observed as a small white shadow having an approximate conical structure. Further, the tumor shadow shown in FIG. 17(*b*) is a lump having a certain size and on the mammogram, it is observed as a whitish round shadow having nearly Gauss distribution.

As described above, listed as main observations of breast cancer are said tumor shadows and said clustered microcalcifications. Detection methods of the tumor shadows include a method in which detection is carried out by comparing the left and right breasts (Med. Phys., Vol. 21, No. 3, pp. 445–452), a detection method employing an iris filter (Singakuron (D-11), Vol. J75-D-11, no. 3, pp. 663–670, 1992), a detection method employing a Quoit filter (Shingakuron (D-11), Vol. J76-D-11, no. 3, pp. 279–287, 1993), a detection method in which binarization is carried out based on the histogram of pixel values in separate breast regions (JAMIT Fontier 95 Proceeding, pp. 84–85, 1995), a minimum direction difference filter which takes the minimum output of a number of oriented Laplacean filters (Shingakuron (D-11), Vol. J76-D-11, no. 2, pp. 241–249, 1993), and the like.

Further, detection methods of the clustered calcification include a method in which a region having a suspicious calcification is localized in the breast region, and pseudo-positive candidates are eliminated based on the optical density difference of shadow images, the standard deviation of boundary density differences, and the like (IEEE Trans. Biomed. Eng. BME-26 (4): 213–219, 1979), a detection method employing images which have been subjected to Laplacean filter treatment (Shingakuron (D-11), Vol. J71-D-11, no. 10, pp. 1994–2001, 1988), a detection method in which, in order to minimize effects of background patterns such as mammary glands, images which have been subjected to morphology analysis are employed (Shingakuron (D-11), Vol. J71-D-11, no. 7, pp. 1170–1176, 1992), and the like.

Images are subjected to image processing, employing image processing means 604, and subsequently displayed. Image processing items, which are carried out employing said image processing means 604, include any one of gradation processing, frequency enhancement processing, and dynamic range compression processing. Said gradation processing comprises an image processing characterized in that specifically, clustered microcalcifications are outputted under the stable contrast wherever said clusters are present in breasts. Further, said frequency enhancement processing comprises one characterized in that specifically, a distance function is prepared employing the skin lines, and the dynamic range is compressed based on the resulting function. Furthermore, said image processing is characterized in that it is carried out under the same conditions for the same direction and/or the same breast of one patient. Further, the image processing conditions may be determined for each image or may be determined according to the previously determined conditions.

When a plurality of images is simultaneously displayed in said image displaying means, it is preferable that all images be subjected to image processing under the same conditions.

a. Gradation Processing

In gradation processing, a gradation conversion curve, which shows the relationship between original image data (input) and gradation processed image data (output), is determined based on the analytical results of image data, and the gradation processing is carried out employing the resulting gradation conversion curve.

Prior to said gradation processing, when an irradiated field recognition processing, which detects the radiation irradiated region, is carried out, various image processing conditions are preferably set utilizing the image data in the perceived irradiated field region so as to properly carry out image processing of an image area required for diagnosis.

Based on Medical Imaging Technology, Vol. 14, No. 6, November 1996, pages 66 to 671, a contrast correction curve is prepared which is capable of correcting the contrast of microcalcification images locating in various regions to approximately the same level. By converting pixel values of all pixels on the breast region image, utilizing said correction curve, correction is carried out so that the density gradation of the low-density region of contrast decreasing fibroglandular tissue and mass is expanded, and by contrast, the density gradating of the fatty region, in which the possibility of the presence of microcalcification images is small, is compressed.

Said contrast correction processing contributes to an improvement of automatic detection performance, as well as being effective for easier observation of the interior of the fibroglandular organ. Accordingly, it is possible to apply it to a image processing method.

b. Frequency Enhancement Processing

In frequency enhancement processing, it is possible to control the sharpness of images employing means such as a unsharp mask processing, multiple-resolution method, and the like.

c. Dynamic Range Compression Processing

In dynamic range compression processing, it is possible to compress the dynamic range in an optional signal region, employing methods described in Japanese Patent No. 2509503 or 2663189. As another example, a distance function is prepared employing skin lines in a mammogram and dynamic compression is carried out based on said distance function.

Since the density adjacent to the skin line is very high, the details tend to be lost in the solid black. This is due to the fact that in a mammogram imaging method, a breast is imaged while clamped. When the breast is imaged while clamped, the thickness of the breast adjacent to the skin line is not so large, so that X-rays are transmitted through a thinner body portion compared to other portions, thereby resulting in higher transmittance. Further, approaching the skin line, the thickness of the breast decreases. Accordingly, a distance function, which varies depending on distance, is prepared, and the dynamic range is compressed by decreasing the pixel value adjacent to the skin in accordance with said distance function. A processing condition varying means may be provided so that varied conditions are stored employing said means.

In image output control signal inputting means 603, by utilizing a mouse attached to image displaying means 608, for example, the contrast of the region in which the gradation is variable and disease may be caused, is increased. As a result, it is possible to vary the gradation for easier diagnosis. In this case, when the mouse is moved vertically, the contrast varies continuously, while when it is moved horizontally, the brightness varies continuously. As a result, it is possible to readily adjust the image to the desired gradation. Further, by operating said mouse, in addition, it is possible to carry out image magnification factor processing, image switching, alteration of gradation, and the like. The magnification of images is carried out employing appropriate hardware, and it is possible to immediately magnify the image or an optional magnification factor by moving the mouse around the position guided by a pointer. Further, since interpolation processing is carried out, a mosaic shape is not formed by magnification and thus diagnosis is more readily carried out. Image processing conditions, which are determined as above, may be stored.

For example, when radiation images of a group examination are diagnosed, each radiation image is diagnosed within 5 to 20 seconds, and continuously switched to the subsequent image. Image switching is immediately carried out by pointing a button-shaped region located in the upper right of the image with a pointer and depressing the button of the mouse. Commonly, images are only switched sequentially in order. However, it is possible to switch to the previous image by clicking the neighboring region.

A doctor diagnoses radiation images with respect to displayed image data. When an abnormality is found as the result of diagnosing images, input is carried out by pointing to the abnormal location on the image. It may be constituted in such a manner that inputted diagnostic information is stored in the diagnostic information storing means.

Employed as image displaying means 608 may be any ordinary image displaying means, known in the art, such as CRTs, liquid crystal displays, plasma displays, and the like. Among those, special CRTs or liquid displays for medical use, which exhibit high accuracy and high luminance, are most preferred. Further, the number of display pixels of the display with high accuracy is preferably at least approximately 1,000×1,000, and is most preferably at least approximately 2,000×2,000.

Further, a display controlling number storing means is provided which controls the display position of each image, the reversal of each image, and the rotation of each image. Accordingly, it is possible to compare and check each displayed image from various directions while controlling its displayed position, its reversal, and its rotation. As a result, it is possible to easily, quickly, and accurately carry out medical image diagnosis employing images.

Image output controlling means 610 inputs images to image displaying means 608, or image printing means 609, based on image output controlling signals of image output controlling signal inputting means 603.

Figure 18:
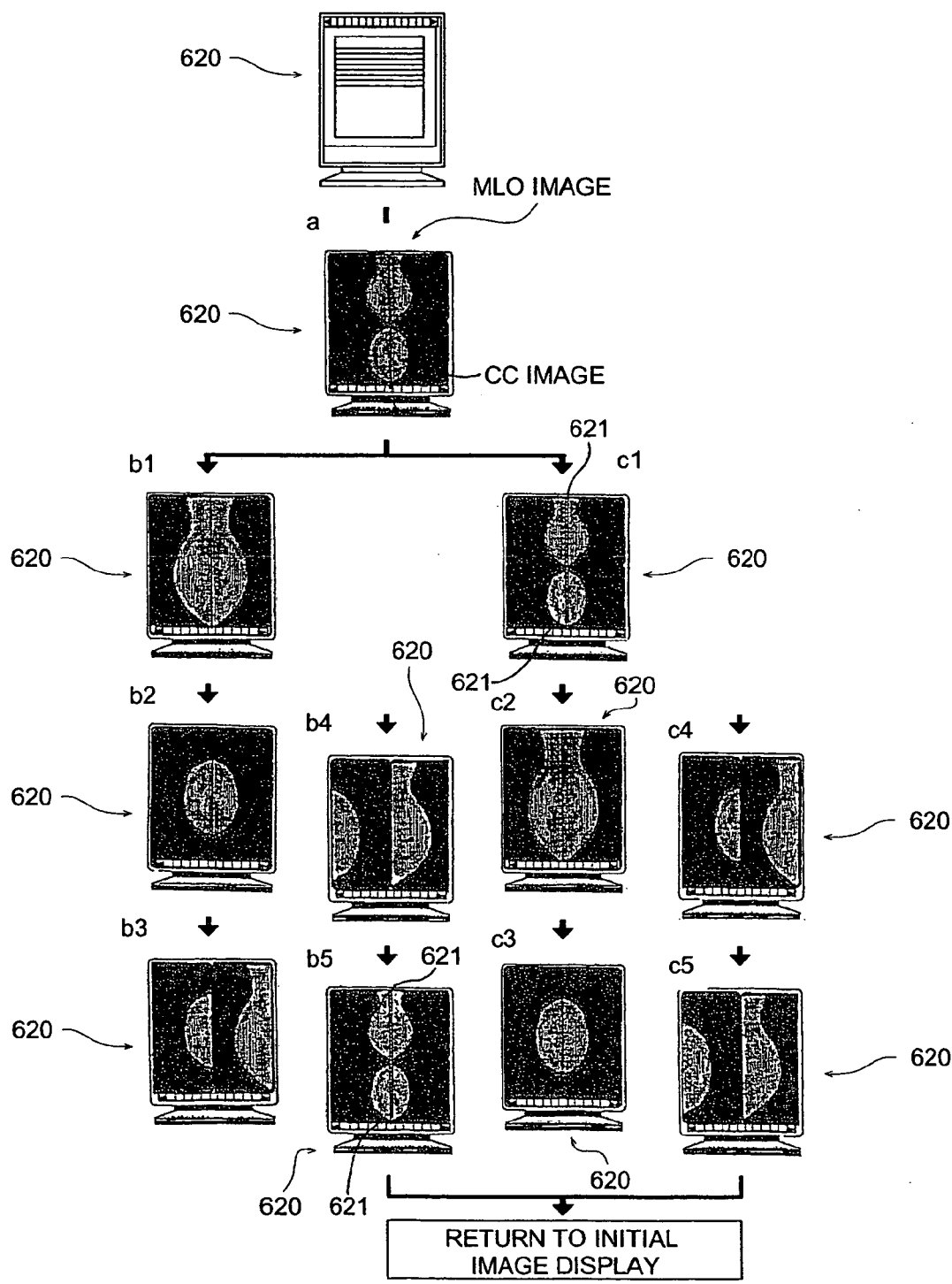
FIG. 18 is a series of displays showing image switching.

Image data, which are read out from image storing means 605, are displayed in image displaying means 608. Said image displaying means 608 switches images as shown in FIG. 18. Said means comprises an all-image display mode which simultaneously displays all mammogram images, and a group display mode which divides all images into at least two groups and displays the images included in each group. Further, said means comprises a mode switching means which switches said modes.

In the present embodiment, a display mode switching means is provided, which switches image display modes in a previously specified order, and displays the resulting mode. CRT 620 displays images in the following manner. The first display shows a left and a right breast. which are imaged in the same direction, and face each other. For example, the CC images of the left and right breast which are imaged in the vertical direction are face each other. Further, a 4-division display (an all image display) is shown in which MLO images, which are imaged in the oblique direction, face each other. Subsequently, the following displays are shown. Images are divided into two series. In series "b", display b1 is a 2-division display (group display) in which MLO images of the left and right breast face each other. Display b2 is a 2-division display in which CC images of the left and right breast face each other. Display b3 is a 2-division display in which the CC image and the MLO image of the right breast face each other. Display b4 is a 2-division display in which the CC image and the MLO image of the right breast face each other. Display b5 is the final 4-division display in which the CC images of the left and right breast are face each other and the MLO images of the same face each other. Marker 621 is attached to the abnormal shadow candidate position of the images and is displayed. Subsequently, the display returns to the initial image display.

Further, in series "c", display c1 is a 4-division display in which the CC images of the left and right breast face each other and the MLO images of the same faced, and marker 61 is attached to the abnormal shadow candidate position of said image and displayed. Display c2 is a 2-division display in which the MLO images of the left and right breasts are faced. Display c3 is a 2-division display in which the CC images of the left and right breast face each other. Display c4 is a 2-division display in which the CC image and the MLO image of the right breast face each other. Display c5 is a 2-division display in which the CC image and the MLO image of the left breast face each other. Subsequently, the display returns to the initial image display.

The two series, "a" and "b", differ on the point in which an abnormal shadow detecting means is displayed in an early stage or in a later stage. When displayed in the early stage, it serves to reduce the load on doctors since it is possible for doctors to very carefully read the detection results of abnormal shadows pointed out by the computer. When displayed in the later stage, it results in double reading and serves to minimize oversight, since abnormal shadow detection results are displayed after doctors have made their diagnosis. Further, it is possible to select one of two series, depending on doctors' preference, as well as diagnosis situations, so that diagnostic performance is optimized.

Further, images included in one group are at least two images of the left breast of one patient which are imaged from different directions, at least two images of the right breast of one patient which are imaged from different directions, or at least two images of the left breast and the right breast of one patient which are imaged from different directions, or at least two images of the left breast and the right breast of one patient which are imaged from the same direction.

As described above, by simultaneously displaying all images, including all mammogram images, and by displaying a group which includes images which are obtained by dividing all images into at least two groups, including a plurality of said images, it is possible to read images in a specific group while diagnosing them, and to quickly and accurately diagnose said images.

Further, a display mode switching means is provided, and images are displayed upon switching image display modes in accordance with the previously specified order. Accordingly, for example, foreknowledge is not given to doctors or images can be compared without missing any image. Thus, it is possible to readily, quickly, and accurately carry out medical image diagnosis.

Further, a diagnosis order storing means is provided which previously stores image the diagnosis sequence and images are displayed upon switching the display mode in accordance with said image diagnosis order. As described above, said diagnosis sequence is previously stored and images are displayed upon switching the display modes in accordance with said diagnosis sequence. Accordingly, it is possible for doctors to set the sequence based on the preference of each doctor and to diagnose images. As a result, it is possible to improve diagnostic performance, as well as to quickly and accurately carry out image diagnosis.

Figure 19:
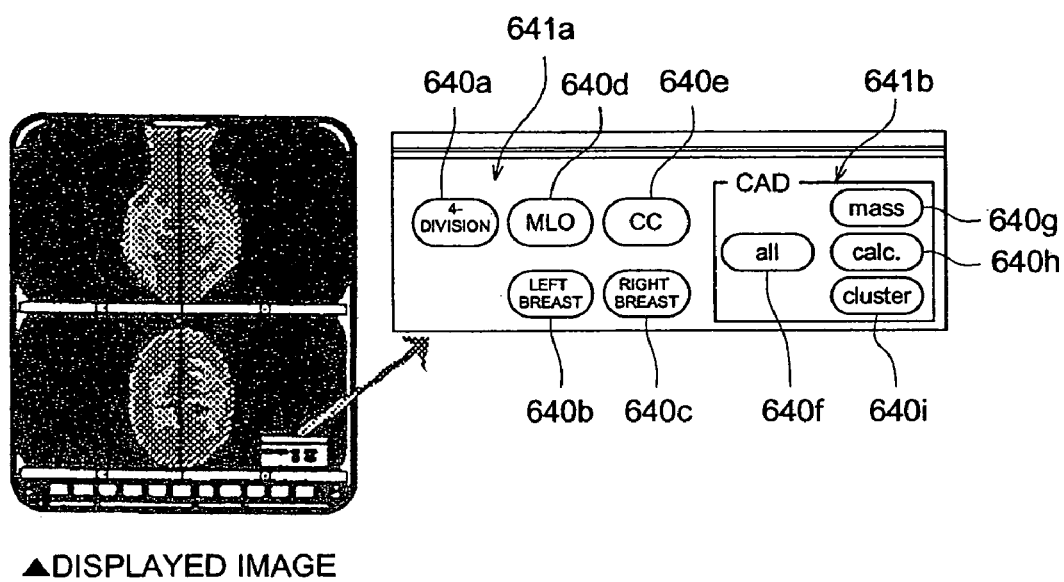
FIG. 19 is a view explaining display operation.

Still further, said image displaying means 608 is provided with operation display 640 comprised of a touch panel shown in FIG. 19. Provided on said touch panel are 4-division display key 640*a*, right breast display key 640*b*, left breast display key 640*c*, MLO image display key 640*d*, CC image display key 640*e*, all detection display key 640*f*, mass display key 640*g*, calc. display key 640*h*, and cluster display key 640*i*.

By operating display mode selecting means 641*a* employing said 4-division display key 640*a*, right breast display key 640*b*, left breast display key 640*c*, MLO image display key 640*d*, CC image display key 640*e*, and the like, it is possible to plan and input the arrangement of the image displays required for image diagnosis and to optionally select each imaging direction and display direction. As described above, it is possible to plan and input the arrangement of the image displays required for image diagnosis and to optionally select each imaging direction and display direction. Accordingly, for example, it is possible for doctors to optionally display desired images, and the like, and to carry out comparison and the like. Thus it is possible for doctors to readily, quickly, and accurately carry out medical image diagnosis.

Further, by utilizing detection result display means 641, such as all detection display key 640*f*, mass display key 640*g*, calc. display key 640*h*, cluster display key 640*i*, and the like, mammogram detection results are displayed. Said all detection display key 640*f* displays all detection results. By operating mass display key 640*h*, microcalcification detection results are displayed, while by operating cluster display key 640*i*, clustered microcalcification detection results are displayed.

Further, after displaying detection results by depressing the necessary keys, by making it possible to readily delete the displayed results by depressing the same key, only desires results are displayed, which is more convenient for diagnosis.

Further, by making it possible to select one of the switching methods in which the image display modes are switched in accordance with a previously specified sequence and a switching method in which switching is carried out to the display mode selected by said display mode selecting means 641*a*, for example, foreknowledge is not given to doctors or images can be compared without missing any image. Thus, it is possible to readily, quickly, and accurately carry out medical image diagnosis.

Further, patient information, as well as examination information corresponding to images, is stored and a plurality of images of one patient as well as one examination are displayed. Accordingly, for example, by comparing each of the images, it is possible to readily, quickly, and accurately carry out image diagnosis employing said medical images.

Patient information images are preferably tinted relatively darkly. When brightly tinted, doctors may suffer from eye fatigue and diagnosis performance may be degraded.

Further, regarding images included in a group of images of one patient or one examination, it is possible to determine the displayed position or displayed image direction corresponding to the imaging direction, as well as the right or left breast. Thus, by comparing and diagnosing images from various directions, it is possible to readily, quickly, and accurately carry out image diagnosis employing medical images.

Figure 20:
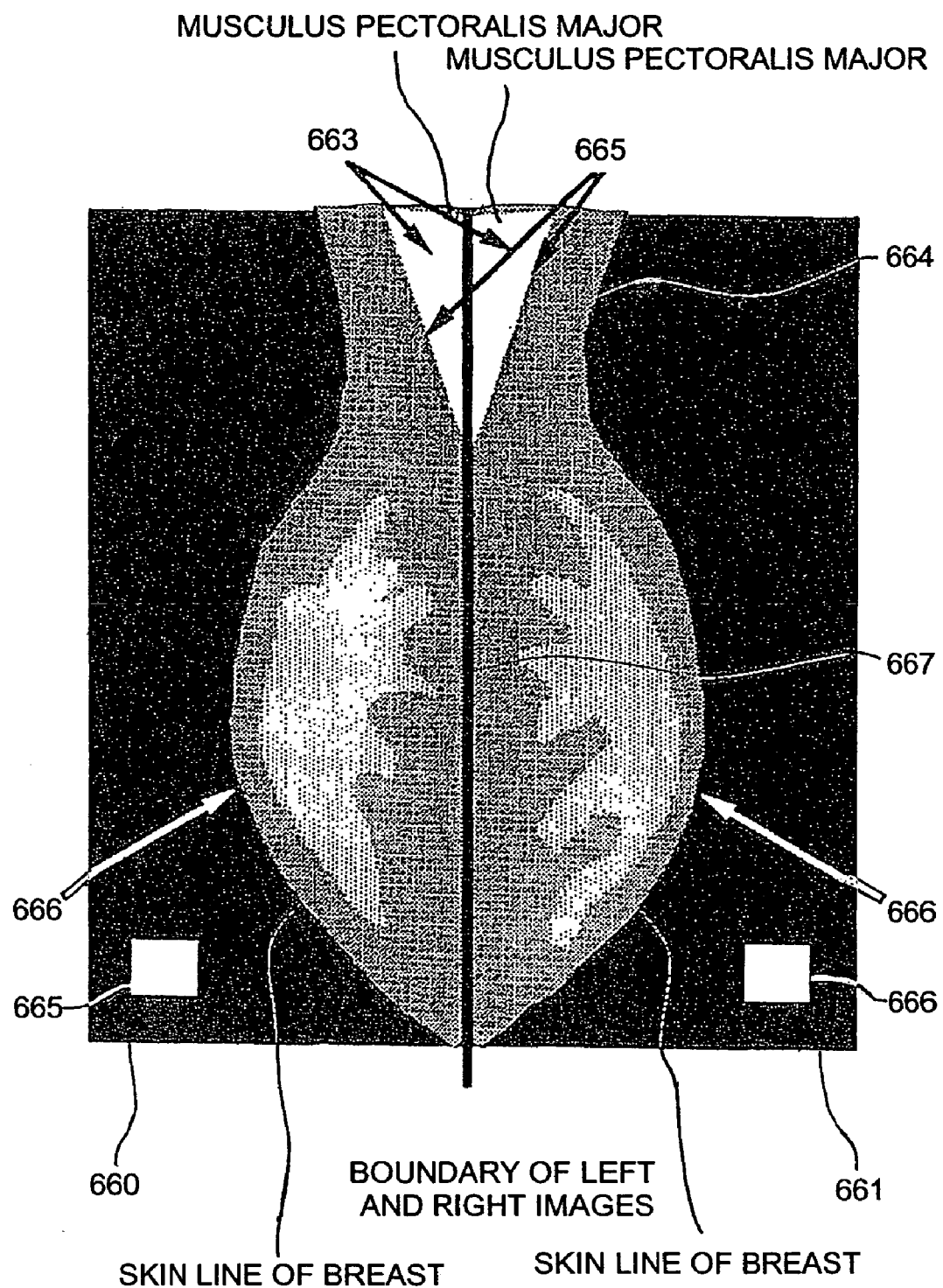
FIG. 20 is a view in which the left breast image and the right breast image of one patient in the same radiography direction are arranged at right and left so that both nipples are directed outward.

Further, as shown in FIGS. 18 and 20, it is possible to display images of the left breast and the right breast of one patient which are imaged in one direction which are arranged in a row so that each nipple is directed outward. As described above, by displaying images of the left breast and the right breast of one patient while imaged in one direction, which are arranged in a row, so that each nipple is directed outward, each image is compared. As a result, it is possible to readily, quickly, and accurately carry out image diagnosis.

Further, the nipple side is trimmed. By trimming the nipple side as above, it is possible to reduce the image size. As a result, displaying speed increases and memory is saved. Further, by displaying patient information 55 in a part of the region in which the imaging object of the nipple side is not imaged, employing an overlay, it is possible to display the patient information while it is not overlapped with the imaging object. As a result, it is possible to readily and accurately carry out image diagnosis.

Further, the position of the left and right breast is matched in the vertical direction. By matching the positions of the left and right breast in the vertical direction, images are accurately displayed in a symmetrical state, and the left and right breast are readily compared. As a result, it is possible to anticipate improvement of diagnostic performance.

Said position matching of the left and right breast in the vertical direction is carried out employing an automatic position matching means. In this embodiment, as shown in FIG. 20, the positions of the right and left breast imaged in the same direction are matched based on skin lines 660 and 661 in the image. In images captured in the same direction, said skin lines 660 and 661 are approximately symmetrical with respect to the direction of chest wall 667. It is possible to compare the shape of said skin line, and to match the left and right breast at the position at which cumulative absolute value difference of the distance from the chest wall in the same row to the skin line and the like. Further, by utilizing boundary 664 between pectoral region 663 and breast region 664, it is possible to match positions in the same manner. By utilizing such a position matching means, it becomes relatively easy for doctors to diagnose images, whereby more accurate diagnosis is anticipated.

Further, by analyzing image data or labeling identification, an imaging direction discriminating means is provided which automatically discriminates the imaging direction of MLO images, as well as CC images, and left and right breast discriminating means which automatically discriminates the left and right breast, utilizing identification labels. It is unnecessary for operators to divide images into groups when desired. Accordingly, since images are readily and suitable divided into groups, it is possible to quickly and accurately carry out diagnosis.

Figure 21:
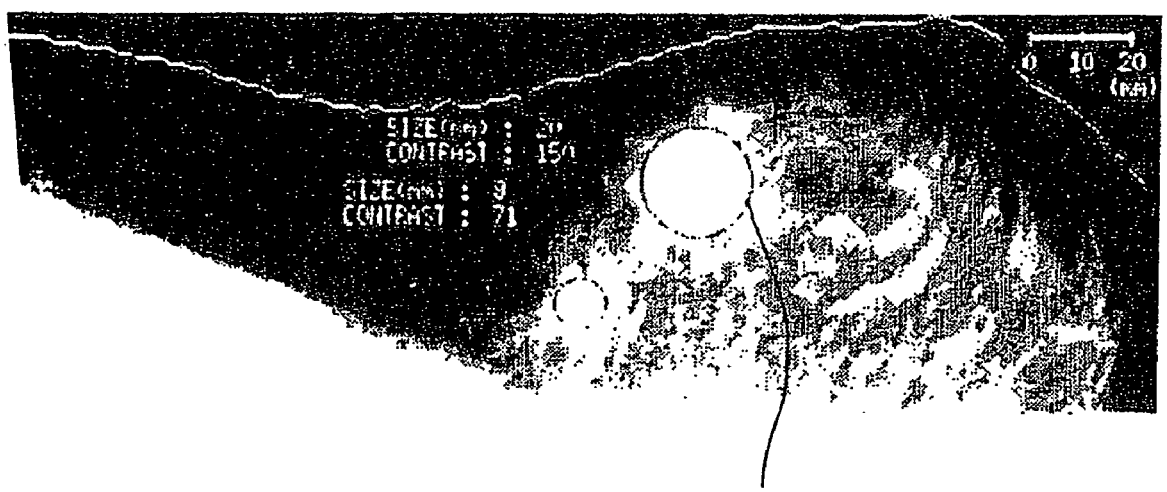
FIG. 21 is a view showing an example in which a circle is drawn at the abnormal shadow candidate position of a mass detection of tumors.
Figure 22:
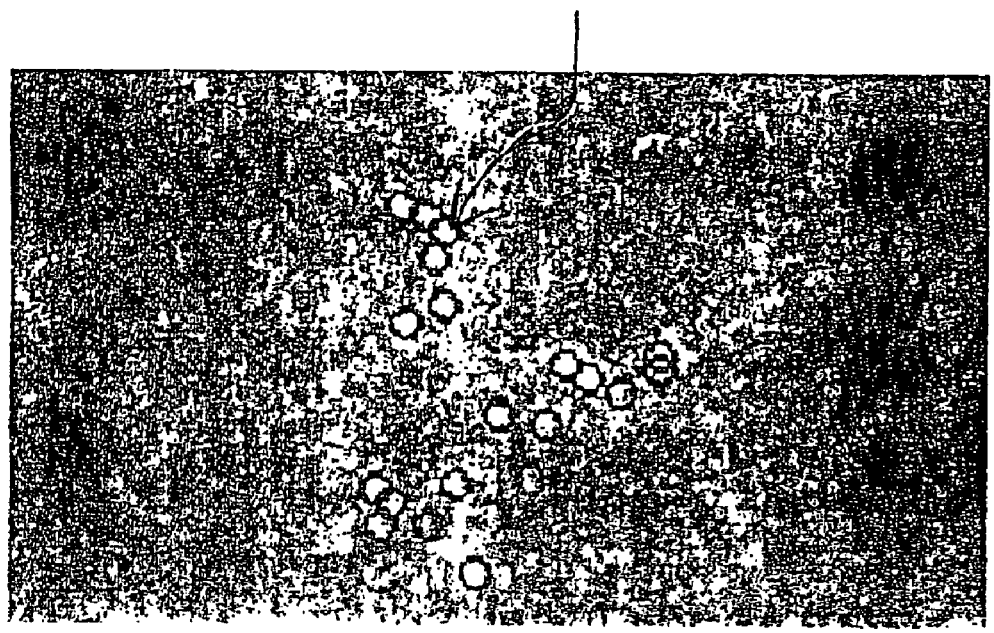
FIG. 22 is a view showing an example in which markers are drawn at abnormal shadow candidate positions of the calc detection of microcalcifications.
Figure 23:
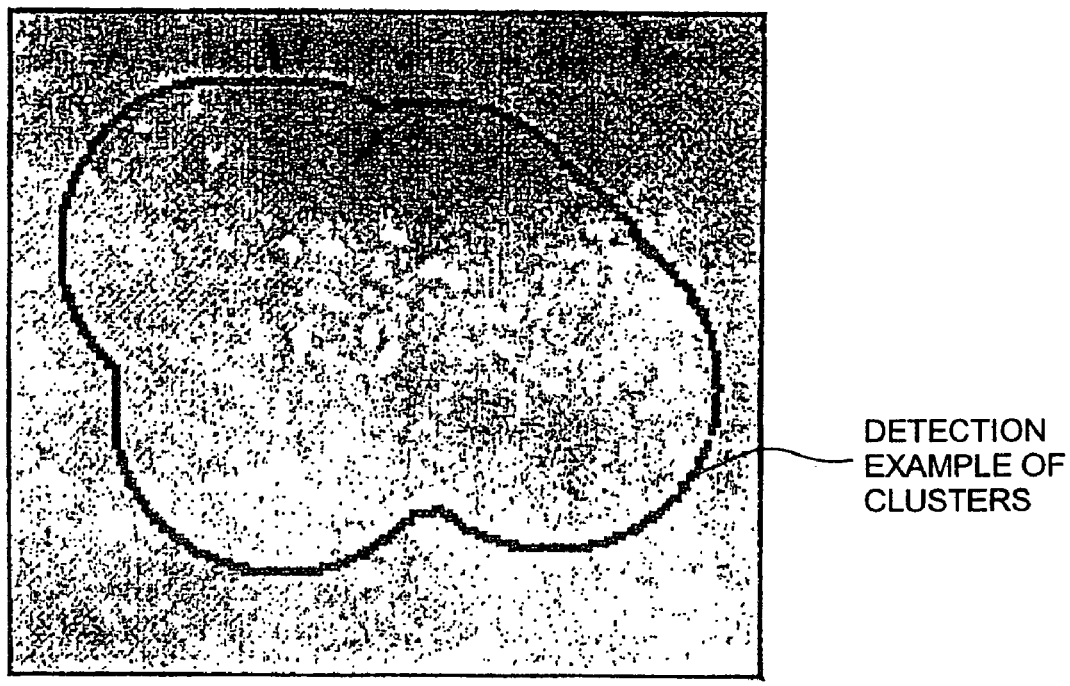
FIG. 23 is a view showing an example in which a marker is drawn around the abnormal shadow candidate region of microcalcification cluster detection.

Further, abnormal shadow candidate detecting means 606 is provided which detects abnormal shadow candidates. Information detected by said abnormal shadow candidate detecting means 606 is stored employing abnormal shadow storing means 607. As described above, abnormal shadow candidates of images are detected and said abnormal shadow candidates are displayed. As shown in FIGS. 21 through 23, in the display of said abnormal shadow candidates, markers are attached to positions of abnormal shadow candidates. FIG. 21 shows an example in which a marker is attached to the abnormal shadow candidate, indicating that the mass of tumor shadow has been detected. FIG. 22 shows an example in which markers are attached to abnormal shadow candidates in which microcalcifications have been detected. FIG. 23 shows an example in which a marker is attached to the abnormal shadow candidate in which microcalcification clusters have been detected. Positions of such abnormal shadow candidates of images are displayed while attached to markers. As a result, it is possible to simply and securely identify abnormal shadows and to accurately carry out image diagnosis. The shapes of said markers are not limited to those shown in FIGS. 21 through 23, and for example, arrow markers may be employed. Further, the shape as well as color may be varied in accordance with various types of abnormal shadows.

Further, as shown in FIG. 24, it is possible to attach scale 670 to the image. By attaching said scale 670 to the image, it is possible to more readily determine the size of, for example, abnormal shadows and the like.

Figure 25:
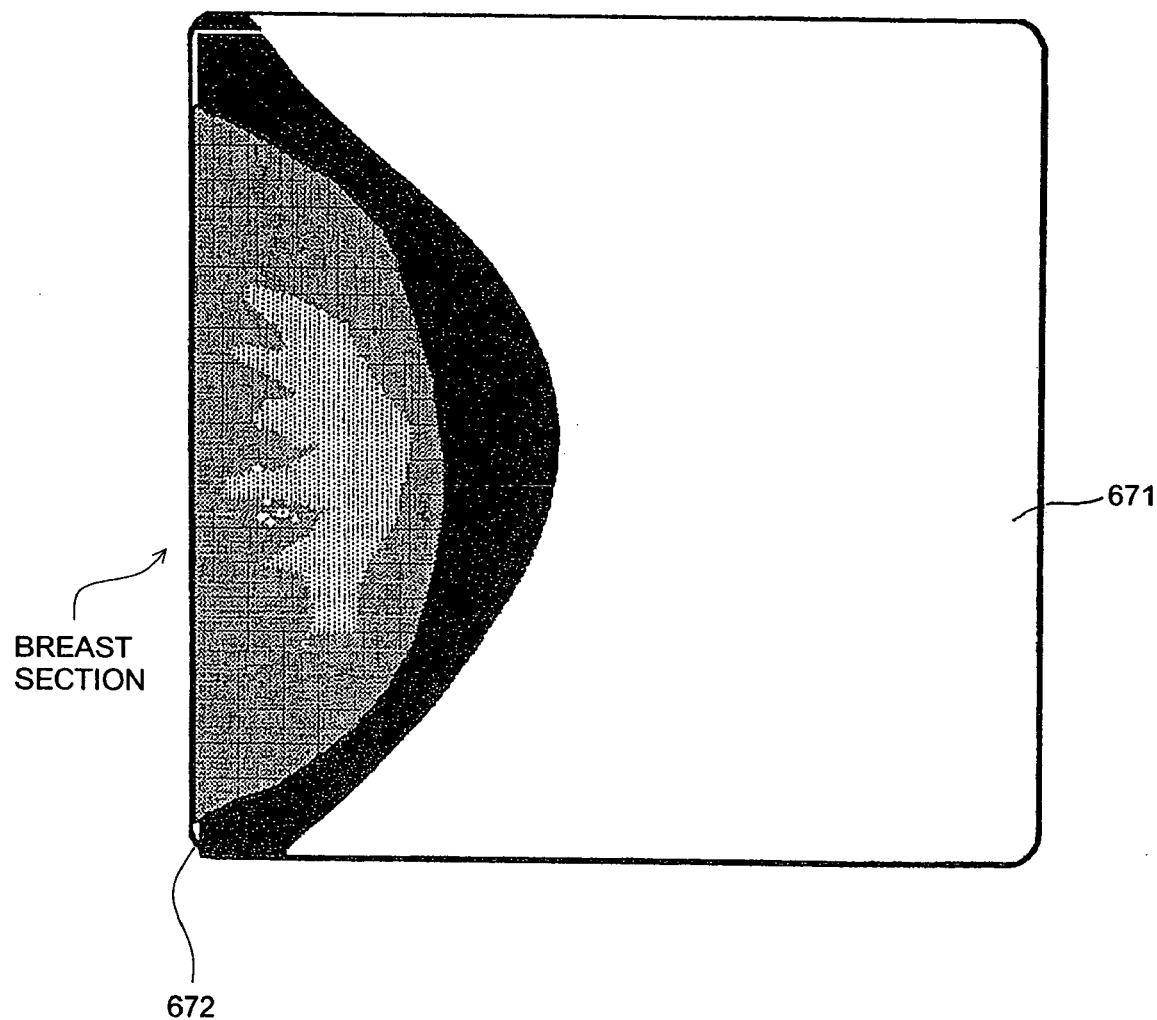
FIG. 25 is a view showing a state in which a white region, a transparent region, and the like, are formed due to the presence of a lead plate during radiography.

Furthermore, during imaging, as shown in FIG. 25, white region 671, transparent region 672, and the like are formed due to shielding materials such as lead plates and the like. When said white region is large, it is difficult for doctors to read shadows. Accordingly, the region shielded by lead in the image is. blackened in solid and displayed. As described above, since the image part shielded by lead is blackened in solid and displayed, it is possible to anticipate a decrease in eye fatigue, and it is also useful to improve shadow reading performance.

Further, as shown in FIG. 26, the interior region and the exterior region of magnification factor display window 681 are subjected to different image processing, and it is possible to make the abnormal shadow of said magnification factor display window 681 more marked. Accordingly, it is possible to readily, accurately, and quickly detect abnormal shadows.

Said image processing comprises gradation processing, frequency enhancement processing, dynamic range compression processing, and interpolation processing processing, each of which has been detailed.

For example, the interior region and the exterior region of magnification factor display window 681 are subjected to different gradation processing. Specifically, a gradation processing look-up table corresponding to each of the different gradation conversion curves is previously stored with respect to the interior region and the exterior region of magnification factor display window 681, and processing data, which are obtained referring to each of the gradation processing look-up tables, are displayed. At that time, the contrast of the gradation conversion curve corresponding to the interior region of said magnification factor display window is preferably higher than that of the gradation conversion curve corresponding to the exterior region of the same.

Further, instead of beforehand determining the gradation conversion curve corresponding to the interior region of the magnification factor display window, when said magnification factor display window is decided on, image data in said magnification factor display window may be statistically analyzed and a graduation conversion curve may be prepared based on the results. Specifically, the contrast of the gradation conversion curve is determined so that the approximate maximum value, as well as the approximate minimum value, of image data in the magnification factor display window are displayed at the specified luminance; signal values are obtained so that the cumulative histogram value of image data in the magnification factor display window reaches the specified value and the gradation conversion curve is prepared so that the resulting signal values are displayed at the specified luminance; or the histogram of image data in the magnification factor display window is calculated and the gradation conversion curve is prepared, based on the histogram equalization method known in the art.

Further, only the interior region of the magnification factor window may be displayed employing the gradation in which black and white are reversed.

In another example, the interior region and the exterior region of the magnification factor display window 681 are subjected to different frequency enhancement processing. For example, when a unsharp mask processing method is employed as said frequency enhancement processing, different mask sizes as well as different enhancement coefficients are previously stored with respect to the interior region and the exterior region of the magnification factor display window, and processing data, which are calculated while utilizing each different mask size and enhancement coefficient are displayed. When a multiple resolution method is employed as the frequency processing, different enhancement frequency bands as well as enhancement coefficients are previously stored with respect to the interior region and the exteriors region of the magnification factor display window, and processing data are displayed which are calculated while utilizing each enhancement frequency band as well as each enhancement coefficient. In these cases, the enhancement coefficient corresponding to the interior region of the magnification factor display window is preferably greater than the corresponding exterior region of the same. Further, frequency enhancement processing conditions are preferably determined so that the enhancement frequency corresponding to the interior region of the magnification factor display window is higher than the corresponding exterior region of the same.

In still another example, the interior region and the exterior region of the magnification factor display window 681 are subjected to different dynamic range compression processing. For example, the exterior region of magnification factor window display 681 is only subjected to dynamic range compression processing, while the interior region of the same is not subjected to said dynamic range compression processing.

Furthermore, when the matrix size of image data is different from that of the display region during the displaying of image displaying means 8, interpolation processing is required. Employed as interpolation processing methods may be interpolation processing calculating methods such as nearest neighbor interpolation processing, straight-line interpolation processing, spline interpolation processing, cubic-convolution interpolation processing, or bell-spline interpolation processing, and the like (refer to IEEE Trans. on Acoustics and Signal Processing, Vol. ASSP=29, No. 6, 1981, IEEE Trans. on Medical Imaging, Vol. M1–2, No. 3, 1983, SPIE Proc. M1–11, 1988). The degree of an interpolation processing function employed in interpolation processing calculation is, for example, 0 degree in the nearest neighbor interpolation processing, 1 degree in the straight-line interpolation processing, 3-degree in the spline interpolation processing, cubic-convolution interpolation processing, and the like. Generally, when higher degree functions are employed, it is possible to minimize the degradation of image information due to the interpolation processing processing.

As described above, by carrying out image processing such as the gradation processing, frequency enhancement processing, dynamic range compression processing, interpolation processing processing, and the like, it is possible to readily, accurately, and even quickly detect abnormal shadows.

Further, image processing conditions are determined based on magnification factor. Generally, of the same images, an image having less magnification factor results in a visually higher contrast. Due to that, when the magnification factor is increased, the contrast is increased; when the magnification factor is increased, the degree of enhancement of the frequency enhancement processing is increased; and when the magnification factor is increased, the degree of the interpolation processing function of the interpolation processing is increased. Since image processing conditions are determined based on the magnification factor, image disorder and the degradation of information due to magnification factor are minimized. As a result, it is possible to readily, accurately, and even quickly detect abnormal shadows.

Specifically, since microcalcifications result in low contrast of imaging objects compared to cancer shadows, the contrast of the gradation conversion curve corresponding to microcalcifications are increased more than that of the gradation conversion curve corresponding to cancer. Further, since microcalcification comprises higher frequency structures compared to cancer, the enhancement coefficient of the frequency enhancement processing corresponding to microcalcification is increased more than that of cancer. The major enhancement frequency of the frequency enhancement processing corresponding to microcalcification is increased further than that corresponding to cancer.

Further, the size of magnification factor display window 681 is determined based on the size of abnormal shadow candidates. In this example, the size, which can display entire tumors, is set, while the size, which can displays all microcalcification shadows included in clustered microcalcification is set. Since the size of said magnification factor display window 681 is determined based on the size of abnormal shadow candidates, abnormal shadows are readily observed.

Further, the magnification factor of images is determined based on the pixel size of images as well as the resolution of image displaying means 608. Due to that, images are not disordered by the magnification of images and abnormal shadows are readily observed.

Further, the size of images is determined so as to be in integral multiples of the actual size of the original images. For example, it is possible to determine the magnification factor with respect to the actual size utilizing a ratio of monitor size/(monitor resolution×pixel size of inputted image). In diagnosis employing conventional film, image sizes are the same as actual sizes. Accordingly, actual size and sizes in integral multiples tend to intuitively be understood by diagnosing doctors.

Further, when the information regarding the image magnification factor is displayed together with images, the position of abnormal shadows is readily specified, and the size and the like are readily judged. As a result, it is possible to readily, accurately, and even quickly detect abnormal shadows.

For example, the magnification factors, in numerical values, are displayed in a region other than the image displaying region of the monitor. Alternatively, they are displayed at the periphery of the displayed images. Both, the magnification factor in the exterior of the magnification factor display window and the magnification factor in the interior of the same, may be displayed. Further, switching may be carried out in such a manner that while a pointer indicates the exterior of the magnification display window, magnification factor in the exterior of the magnification display window is displayed, and while said pointer indicates the interior of the same, the magnification factor in the interior of the magnification display window is displayed.

As another example, the magnification factor in the interior of the magnification display window is displayed adjacent to magnification display window 681, utilizing numerical values. Alternatively, the magnification factor is displayed at the periphery of magnification display window 681 or is overlapped with the frame surrounding magnification factor display window 681. Further, except for displaying the magnification factor in numerical values, the magnification factor may be displayed utilizing icons such as graphics which vary in size corresponding to the magnification factor, and the like.

Further, by employing the pixel size of images as well as the resolution of image displaying means 608, conversion is made of the magnification factor with respect to the actual size and the resulting magnification factor is displayed. As described above, since conversion is made employing the actual size as the standard, the resulting sizes tend to intuitively be understood by the diagnosing doctors.

A magnification display controlling signal inputting means is provided, which varies the position of magnification display window 681, the size of images in magnification display window 681, the magnification factor of images in magnification display window 681, and image processing conditions of images in magnification display window 681.

Said magnification display controlling signal inputting means is comprised of image outputting signal inputting means 603. Further, employed as magnification display controlling signal inputting means are, for example, a mouse, a keyboard, a touch panel, and the like. For example, scrolling the position of the magnification display window is carried out in synchronization with the movement of the mouse. Continuous change of the magnification factor in the magnification display window is carried out. Gradation processing conditions are continuously changed in synchronization with the movement of the mouse. Specifically, by varying luminance in multiples in synchronization with the horizontal movement of the mouse as well as varying contrast in the synchronization with the vertical movement of the mouse, it is possible to optionally and readily regulate the gradation processing conditions. Alternatively, frequency enhancement processing conditions are continuously varied in synchronization with the movement of the mouse. Specifically, by varying the mask size of unsharp mask in synchronization with the horizontal movement of the mouse, as well as by varying the enhancement coefficient of unsharp mask processing in synchronization with the vertical movement of the mouse, it is possible to optionally and readily regulate frequency enhancement processing conditions.

The state of magnification display needs not be varied continuously, and may be varied stepwise by clicking a mouse button and the like. The gradation may be subjected to black and white reversal by clicking the mouse button. Further, after various magnification display conditions are altered, employing image output controlling signal inputting means 603, which is a magnification display controlling signal inputting means, final magnification display conditions may be assigned to image data by transmitting "definite" signals, and may be stored in image storing means 605.

As described above, in accordance with the state of abnormal shadows and the like, any of the position of magnification display window 681, the size of magnification display window 681, the magnification factor of images in magnification display window 682, and image processing conditions of images in magnification display window 681 are altered so that abnormal shadows are more readily observed. As a result, it is possible to readily, accurately, and more quickly detect abnormal shadows.

Further, markers are attached to positions of abnormal shadow candidates. Examples, in which said markers are attached, are as follows. Markers are attached to abnormal shadow candidates other than abnormal shadow candidates for which magnification display window 681 is set. Markers are attached to abnormal shadow candidates for which magnification display window 682 is scheduled to be set, following the currently set magnification display window. Further, different-shaped markers are attached to each of the different types of abnormalities or each of different degrees of confidence. Different-colored markers are attached to each of the different types of abnormalities or each of the different degrees of confidence. Different-sized markers are attached to each of the different types of abnormalities or each of the different degrees of confidence. Abnormal shadow candidates, to which the magnification display window already applies, and those, to which the magnification display window does not yet apply, are attached with different-colored markers. Further, markers may be employed in other various cases. As described above, markers are attached to positions of abnormal shadow candidates and displayed. As a result, abnormal shadows are more readily found due to the presence of markers, and it is possible to readily, accurately, and even quickly detect abnormal shadows.

In FIG. 26, markers are shown in such a manner that arrow-shaped markers are attached in the region adjacent to the abnormal shadow candidate so as not to overlap. However, markers are not limited to the above examples. As shown in FIGS. 21, 22, and 23, employed may be markers which are closed non-linear lines which surround abnormal shadow candidates. Further, for example, through the selection employing a button mouse set on a drawing, displays with and without markers may be switched.

It is possible to print onto film or sheets of paper images displayed in image displaying means 608 with or without edition.

Image storing means 605 of the phase contrast radiographic image diagnosis supporting apparatus in this embodiment stores phase contrast radiographic image data. Abnormal shadow candidate detecting means 606 detects abnormal shadow candidates upon analyzing phase contrast radiographic image data. Since phase contrast radiographic images are clearer than ordinarily captured images, it is possible to find abnormal shadow images with higher accuracy. Image displaying means 608 displays stored phase contrast radiographic image data as well as detected abnormal shadow candidates.

The embodiment of the phase contrast radiographic image diagnosis supporting apparatus described in claims 54 and 61 will now be described.

Figure 27:
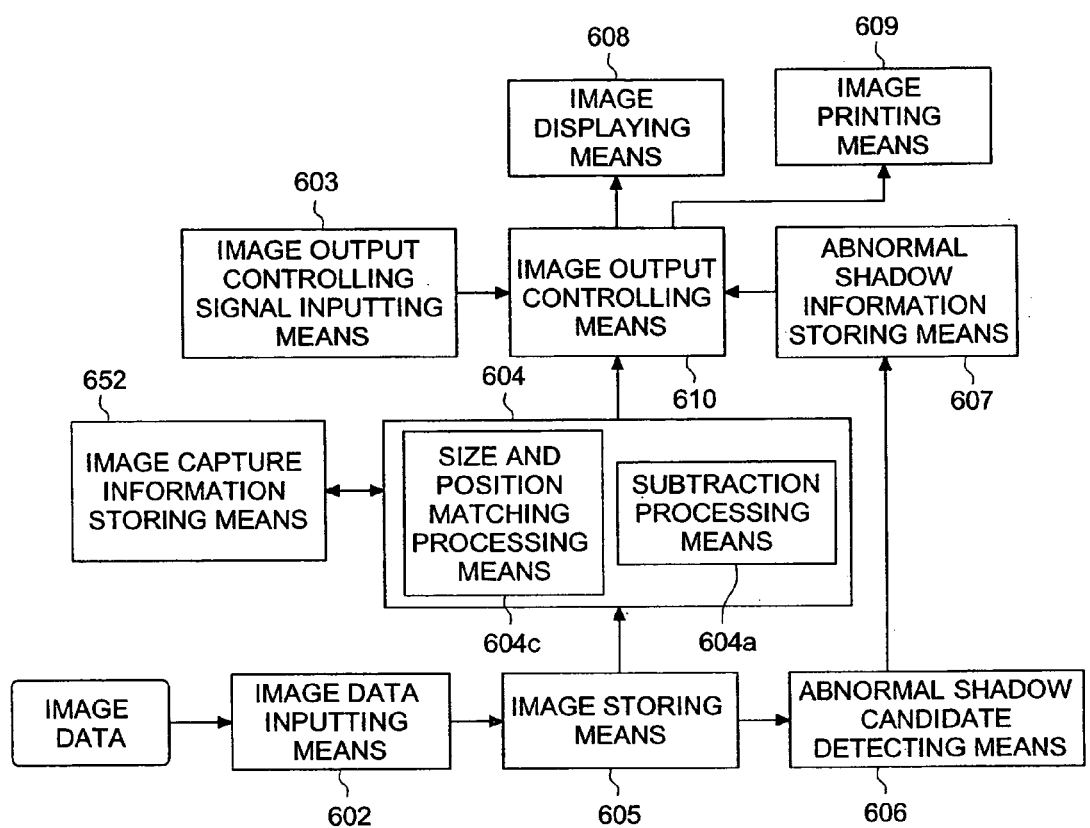
FIG. 27 is a schematic diagram showing another embodiment of an image diagnosis supporting apparatus.

As shown in FIG. 27, the phase contrast radiographic image diagnosis supporting apparatus in this embodiment is constituted in the same manner as embodiments in FIGS. 15 through 26. However, image processing means 604 comprises subtraction processing means 604a and also size and position matching processing means 604c. Since said subtraction processing means 604a and size and position matching processing means 604c are constituted in the same manner as subtraction processing means 150a and size and position matching processing means 150c in the embodiment shown in FIG. 9, description of those is deleted herein.

Since phase contrast radiographic images particularly exhibit excellent depicting capability of blood vessels and the like, it becomes possible to extract the change of a morbid state and the like, utilizing difference with ordinarily capture images. As a result, diagnosis supporting accuracy is enhanced.

The embodiment of the phase contrast radiographic image diagnosis supporting apparatus described in claims 62 and 68 will now be described.

Figure 28:
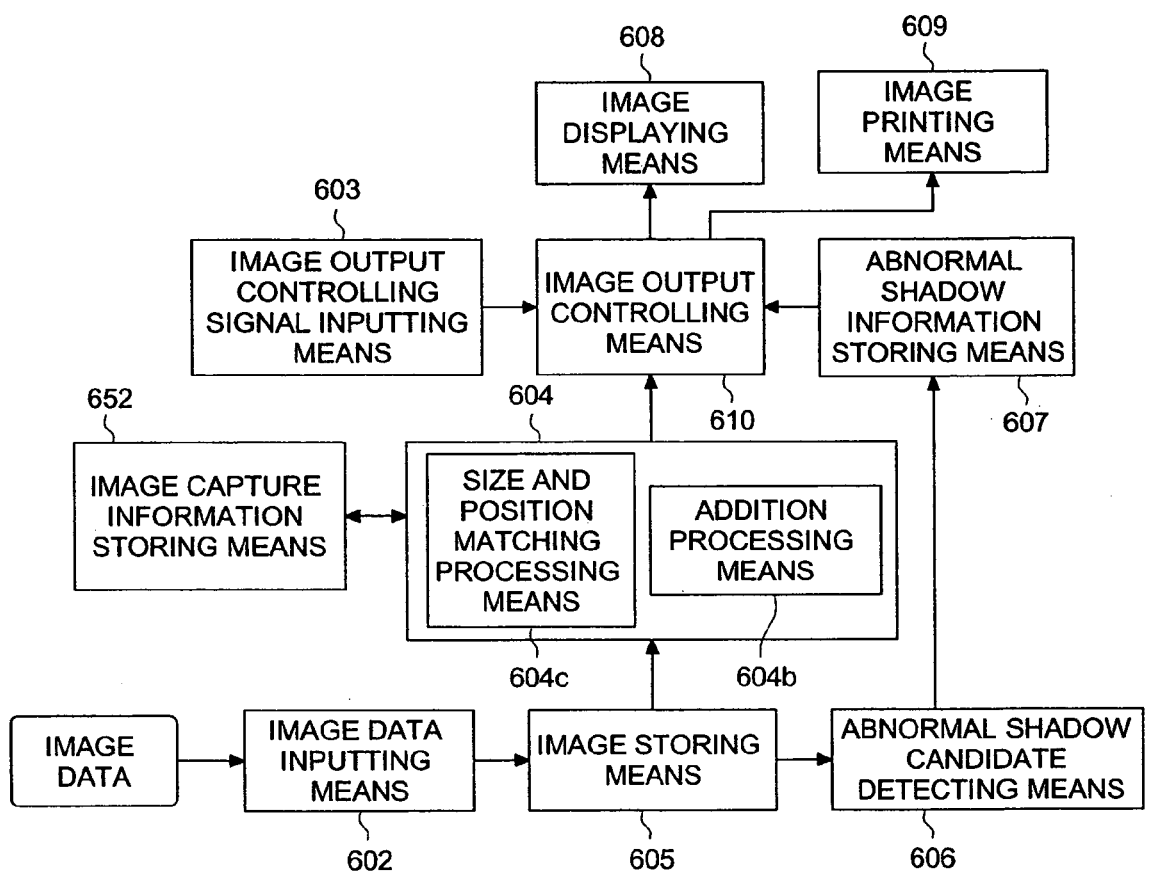
FIG. 28 is a schematic diagram of still another embodiment of an image diagnosis supporting apparatus.

As shown in FIG. 28, the phase contrast radiographic image diagnosis supporting apparatus in this embodiment is constituted in the same manner as the embodiments shown in FIGS. 16 through 26. However, image processing means 604 comprises addition processing means 604b, and also size and position matching processing means 604c. Since said addition processing means 604b and size and position matching processing means 604c are constituted in the same manner as subtraction processing means 150b and position match processing means 150c in the embodiment shown in FIG. 15, description of those is abbreviated herein. It is possible to obtain images with high sharpness employing this embodiment, and further, by performing the addition of images, it is possible to obtain images with less noise components and excellent graininess. As a result, the diagnosis supporting accuracy is enhanced.

Further, the phase contrast radiographic image diagnosis supporting apparatus may comprise the aforementioned subtraction processing means 604a as well as addition processing means 604b so as to make it possible to carry out diagnosis support with higher accuracy.

Further, the present invention is not limited to medical fields, but it is possible to apply the preset invention, for example, to industrial nondestructive inspection.

As described above, in the present invention, comprising an image processing means, which applies image processing to phase contrast radiographic images, makes it possible to apply pertinent image processing to phase contrast radiographic images.

In the present invention, comprising a radiation image detecting means, which outputs image signals corresponding to captured phase contrast radiographic images, as well as an image processing means which applies image processing to signals outputted from said radiation image detecting means, makes it possible to apply pertinent image processing to phase contrast radiographic images.

In the present invention, comprising a subtraction processing means, which obtains subtraction images by applying subtraction processing to a plurality of radiation images comprising at least one phase contrast radiographic image which are obtained by capturing one imaging object, makes it possible to enhance the image quality of energy subtraction.

In the present invention, comprising an addition processing method which obtains addition images by applying addition processing to a plurality of radiation images comprising at least one phase contrast radiographic image which are obtained by capturing one imaging object, makes it possible to enhance the image quality of addition images.

In the present invention, comprising an output means, which outputs phase contrast radiographic images with a reduction factor α of no more than 1, which have been captured under magnification factor, makes it possible to carry out appropriate image output of phase contrast radiographic images.

In the present invention, comprising an image storing means, which stores phase contrast radiographic image data, as well as an abnormal shadow candidate detecting means, which detects abnormal shadow candidates upon analyzing phase contrast radiographic image data, makes it possible to enhance diagnosis supporting accuracy.

In the present invention, comprising a subtraction processing means which obtains subtraction images by applying subtraction processing to a plurality of radiation images comprising at least one phase contrast radiographic image, which are obtained by capturing one imaging object, as well as an abnormal shadow candidate detecting means which detects abnormal shadow candidates upon analyzing said subtraction images, makes it possible to further enhance diagnosis supporting accuracy.

In the present invention, comprising an addition processing means which obtains addition images by applying addition processing to a plurality of radiation images comprising at least one contrast radiographic image which are obtained by capturing one imaging object, as well as an abnormal shadow candidate detecting means which detects abnormal shadow candidates upon analyzing said addition images, makes it possible to further enhance diagnosis supporting accuracy.

What is claimed is:

1. A mammography apparatus for radiographing a breast of a patient, comprising:
    an X-ray tube to emit an X-ray downward,
    an X-ray tube holding section to hold the X-ray tube,
    a breast holding section to hold a breast, the breast holding section located below the X-ray tube holding section, wherein when a focal spot size of the X-ray tube is D(μm), wherein a distance R1 between the X-ray tube and the breast holding section satisfies the following formula:

$$10 \geq R1 > (D-7)/200$$

a detector holding section to hold a detector to detect an X-ray image of the breast, the detector holding section located below the breast holding section with a distance R2 so as to conduct an enlarging radiography of the breast, and
    a supporting section to support and integrate the X-ray tube holding section, the breast holding section, and the detector holding section into one body.

2. The mammography apparatus of claim 1, wherein the breast holding section comprises a flat base on which the breast is placed and the X-ray tube is located vertically above the flat base at an almost patient-side end portion of the flat base.

3. The mammography apparatus of claim 1, wherein the breast holding section comprises a flat base on which the breast is placed and
    wherein when a breast is placed on the flat base, the X-ray tube is located vertically above the flat base at a breast wall-side of the breast.

4. The mammography apparatus of claim 1, wherein the focal spot size D is 10 μm to 1000 μm.

5. The mammography apparatus of claim 4, wherein the focal spot size D is 30 μm to 300 μm.

6. The mammography apparatus of claim 1, wherein the distance R2 between the breast holding section and the detector holding section is 0.15 m or more.

* * * * *